(12) United States Patent
Dow et al.

(10) Patent No.: US 9,320,735 B2
(45) Date of Patent: Apr. 26, 2016

(54) MYELOID DERIVED SUPPRESSOR CELL INHIBITING AGENTS

(75) Inventors: Steven W. Dow, Littleton, CO (US); Angela J Henderson, Fort Collins, CO (US); Leah Mitchell, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/166,017

(22) Filed: Jun. 22, 2011

(65) Prior Publication Data

US 2012/0156280 A1 Jun. 21, 2012

Related U.S. Application Data

(63) Continuation-in-part of application No. 13/050,614, filed on Mar. 17, 2011, now abandoned.

(60) Provisional application No. 61/422,984, filed on Dec. 14, 2010, provisional application No. 61/315,263, filed on Mar. 18, 2010.

(51) Int. Cl.
| | |
|---|---|
| *A61K 39/00* | (2006.01) |
| *A61K 39/39* | (2006.01) |
| *A61K 31/438* | (2006.01) |
| *A61K 31/4184* | (2006.01) |
| *A61K 31/42* | (2006.01) |
| *A61K 31/437* | (2006.01) |
| *A61K 31/5386* | (2006.01) |
| *A61K 39/395* | (2006.01) |

(52) U.S. Cl.
CPC ........... *A61K 31/438* (2013.01); *A61K 31/4184* (2013.01); *A61K 31/42* (2013.01); *A61K 31/437* (2013.01); *A61K 31/5386* (2013.01); *A61K 39/395* (2013.01)

(58) Field of Classification Search
None
See application file for complete search history.

(56) References Cited

U.S. PATENT DOCUMENTS

| | | | |
|---|---|---|---|
| 8,710,191 B2* | 4/2014 | Gladue et al. | 530/388.22 |
| 8,759,014 B2 | 6/2014 | Kammula | |
| 8,975,290 B2 | 3/2015 | Dow et al. | |
| 2002/0042370 A1* | 4/2002 | Hancock | 514/12 |
| 2007/0021466 A1 | 1/2007 | Ungashe et al. | |
| 2007/0025960 A1* | 2/2007 | Pauza et al. | 424/85.2 |
| 2008/0194494 A1 | 8/2008 | Martinez et al. | |
| 2009/0196887 A1 | 8/2009 | Morita et al. | |
| 2014/0248315 A1 | 9/2014 | Dow et al. | |

FOREIGN PATENT DOCUMENTS

| | | |
|---|---|---|
| WO | WO 2005/021708 A2 | 3/2005 |
| WO | WO 2007/124274 A1 | 11/2007 |
| WO | WO 2011/053789 | 5/2011 |
| WO | WO 2011/116299 A2 | 9/2011 |
| WO | WO 2012/030234 | 3/2012 |
| WO | WO2012/054807 * | 4/2012 |
| WO | WO 2012/094703 | 7/2012 |
| WO | WO 2014/134621 A2 | 9/2014 |

OTHER PUBLICATIONS

Brodmerkel et al ( Arthritis and Rheumatism, 2004, v.50, N 9 pp. S263).*
Fridlender et al American Association for Cancer Research, 2009, 70, pp. 109-118.*
Xia, et al., "Recent Developments in CCR2 Antagonists", Expert Opin. Ther. Patents, Johnson & Johnson Pharmaceutical Research and Development, Cranbury, New Jersey, USA, (2009), 19(3):295-303.
Bhangoo, et al., "Delayed Functional Expression of Neuronal Chemokine Receptors Following Focal Nerve Demyelination in the Rat: a Mechanism for the Development of Chronic Sensitization of Peripheral Nociceptors", Molecular Pain, BioMed Central Ltd., 2007, 3:38, pp. 1-20.
Garin, et al., "Chemokines as Targets for Therapy", Experimental Cell 317, ScienceDirect, (2011), pp. 602-612.
International Search Report of PCT/US2011/029022, mailed Dec. 27, 2011, 5 pages.
Written Opinion of the International Searching Authority, 5 pages.
Melani, et al., "Amino-Biphosphonate-Mediated MMP-9 Inhibition Breaks the Tumor-Bone Marrow Axis Responsible for Myeloid-Derived Suppressor Cell Expansion and Macrophase Infiltration in Tumor Stroma", Cancer Research, 2007, vol. 67, No. 23, pp. 11438-11446, ISSN 0008-5472.
Fridlender, et al., "CCL2 Blockade Augments Cancer Immunotherapy", Cancer Research, Jan. 2010, vol. 70, No. 1, pp. 109-118, ISSN 0008-5472.
"The Australasian Gene Therapy Society 4th Society Meeting", The Journal of Gene Medicine, 2005, vol. 7, No. 8, pp. 1113-1143, ISSN 1099-498x.
Dmitry I. Gabrilovich, et al, Coordinated Regulsation of Myeloid Cells by Tumours, Nature Reviews, Immunology, Apr. 2012, pp. 253-268, vol. 12, Macmillan Publishers Limited.
Leah A. Mitchell, et al., Suppression of Vaccine Immunity by Inflammatory Monocytes, The Journal of Immunology, Nov. 7, 2012, pp. 1-10, J Immunol published online.
Leah A. Mitchell, et al., Optimized Dosing of CCR2 Antagonist for Amplification of Vaccine Immunity, International Immunopharmacology, vol. 15, 2013, pp. 357-363, Elsevier.
International Search Report and Written Opinion in International Application No. PCT/US2014/020018, mailed Aug. 13, 2014, 14 pages.

(Continued)

*Primary Examiner* — Michail Belyavskyi
(74) *Attorney, Agent, or Firm* — Cooley LLP

(57) ABSTRACT

Myeloid derived suppressor cell (MDSC) inhibitory agents and vaccine and/or adjuvant enhancers are provided. Improved vaccine treatment regimens employing these agents are also provided. Cancer vaccines and methods for inhibiting tumor growth and cancer metastases are also presented. The myeloid derived suppressor cell (MDSC) inhibiting agents are described as bisphosphonates (such as liposomal clodronate) and CCR2 inhibitors and/or CCR2 antagonists. Methods for enhancing antibody titer levels in response to an antigen of interest are also provided.

6 Claims, 18 Drawing Sheets

(56) References Cited

OTHER PUBLICATIONS

Affolter, V. et al., "Canine Cutaneous and Systemic Histiocytosis", *The American Journal of Dermatopathology* (2000), 22(1): 40-48.
Affolter, V. et al., "Localized and Disseminated histiocytic Sarcoma of Dendritic Cell Origin in Dogs", *Vet Pathol* (2002), 39:74-83.
Aguzzi, A., et al., "Pathogenesis of Prion Diseases: Current Status and Future Outlook", *Nature Reviews, Microbiology* (2006),4:765-775.
Aguzzi, A., et al., "Immune System and Peripheral Nerves in Propagation of Prions to CNS" *British Medical Bulletin* (2003), 66:141-159.
Almand, B., et al., "Increased Production of Immature Myeloid Cells in Cancer Patients: A Mechanism of Immunosuppression in Cancer", *J Immunol* (2001), 166:678-689.
Alves-Rosa, F., et al., "Treatment with Liposome-Encapsulated Clodronate as a New Strategic Approach in the Management of Immune Thrombocytopenic Purpura in a Mouse Model", *Blood.* (Oct. 15, 2000), 96:2834-2840.
Arbel, M., et al., "Generation of Antibodies Against Prion Protein in Wild-Type Mice Via Helix 1 Peptide Immunization", *Journal of Neuroimmunology* (2003), 144:38-45.
Banzhoff, A., et al., "A New MF59-Adjuvanted Influenza Vaccine Enhances the Immune Response in the Elderly with Chronic Diseases: Results from an Immunogenicity Meta-Analysis", *Gerontology* (2003), 49:177-184.
Bird, R., et al., "An Allogeneic Hybrid-Cell Fusion Vaccine Against Canine Mammary Cancer", *Veterinary Immunology and Immunopathology* (2008), 128: 289-304.
Kitawaki et al., "A Phase I/IIa clinical trial of immunotherapy for Elderly Patients with Acute Myeloid Leukaemia Using Dendritic Cells co-Pulsed with WT1 Peptide and Zoledronate," Br. J. Haematology 2011, 153 (6), 796-799.
Brando, C., et al., "Murine Immune Responses to Liver-Stage Antigen 1 Protein FMP011, a Malaria Vaccine Candidate, Delivered with Adjuvant AS01B or AS02A", *Infection and Immunity*, Feb. 2007, p. 838-845.
Bronte, V., "Myeloid-derived suppressor cells in inflammation: Uncovering cell subsets with enhanced immunosuppressive functions", *Eur. J. Immunol.* (2009), 39:2670-2672.
Bucksky, P., et al., "Malignant Histiocytic Disorders in Children, Clinical and Therapeutic Approaches with a Nostalgic Discussion," Hematol Oncol Clin North Am (Apr. 1998), 12:465-471.
Caglar, K., et al., "Effect of monophosphoryl lipid A on antibody response to diphtheria toxin and its subunits", *APMIS* (2005), 113:256-63.
Caughey, B., et al., "Prions and their partners in crime", *Nature* (Oct. 19, 2006), 443:803-810.
Cecchini, M., et al., "Effect of Bisphosphonates on Proliferation and Viability of Mouse Bone Marrow-Derived Macrophages", *Journal of Bone and Mineral Research* (1987), 2(2):135-142.
"Cellular Immunotherapy for Acute Myeloid Leukemia using Dendritic Cells Pulsed with WT1 Peptide and Zoledronate", International Clinical Trials Registry Platform, Jul. 1, 2007, XP002699680.
Clark, R., et al., "Synthesis and Antihypertensive Activity of 4'-Substituted Spiro[4H-3,1-benzoxazine-4,4'-piperidin]-2(1H)-ones", *J. Med. Chem.* (1983), 26:657-661.
Clezardin, P., et al., "In Vitro and In Vivo Antitumor Effects of Bisphosphonates" *Current Medicinal Chemistry* (2003), 10:173-180.
Condamine, T., et al., "Molecular mechanisms regulating myeloid-derived suppressor cell differentiation and function", *Trends Immunol.* (2011), 32(1):19-25.
Desai, M., et al., "Immune response with biodegradable nanospheres and alum: studies in rabbits using staphylococcal enterotoxin B-toxoid", *J. Microencapsulation* (2000), 17(2):215-225.
DeSanto, C., et al., "Nitroaspirin corrects immune dysfunction in tumor-bearing hosts and promotes tumor eradication by cancer vaccination", *National Academy of Sciences of the USA* (Mar. 15, 2005),102(11):4185-4190.

de Souza Matos, D., et al., "Immunostimulatory effects of polar glycopeptidolipids of *Mycobacterium chelonae* for inactivated rabies vaccine", *Vaccine* (2000), 18:2125-2131.
Diaz-Montero, C.M., et al., "Increased circulating myeloid-derived suppressor cells correlate with clinical cancer stage, metastatic tumor burden, and doxorubicin-cyclophosphamide chemotherapy", *Cancer Immunol Immunother.* (Jan. 2009), 58(1):49-59.
Dow, S., et al., "In Vivo Tumor Transfection with Superantigen plus Cytokine Genes Induces Tumor Regression and Prolongs Survival in Dogs with Malignant Melanoma", *J. Clin. Invest.* vol. 101, No. 11, Jun. 1998, 2406-2414.
Eldridge, J., et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies", *Infection and Immunity* (Sep. 1991), 59(9):2978-2986.
Enari, M., et al., "Scrapie prion protein accumulation by scrapie-infected neuroblastoma cells abrogated by exposure to a prion protein antibody", *Proc. Natl. Acad. Sci*. (2001), 98(16):9295-9299.
Extended European Search Report mailed Jul. 8, 2013, in European Application No. EP 11757071.
Flick-Smith, H., et al., "Mucosal or Parenteral Administration of Microsphere-Associated *Bacillus anthracis* Protective Antigen Protects against Anthrax Infection in Mice", *Infection and Immunity* (Apr. 2002), 70(4):2022-2028.
Frith, J., et al., "The Molecular Mechanism of Action of the Antiresorptive and Antiinflammatory Drug Clodronate", *Arthritis & Rheumatism* vol. 44, No. 9, Sep. 2001, pp. 2201-2210.
Frith, J., et al., "Clodronate and Liposome-Encapsulated Clodronate Are Metabolized to a Toxic ATP Analog, Adenosine 5'-(β,γ-Dichloromethylene) Triphosphate, by Mammalian Cells In Vitro", *Journal of Bone and Mineral Research* (1997), vol. 12, No. 9, pp. 1358-1367.
Gabrilovich, D.I. et al, "Myeloid-derived suppressor cells as regulators of the immune system", *Nat Rev Immunol* (Mar. 2009), 9(3):162-174.
Gallaniga, S., et al., "Targeting tumor-associated macrophages and inhibition of MCP-1 reduce angiogenesis and tumor growth in a human melanoma xenograft", *Journal of Investigative Dermatology* (2007), 127:2031-2041.
Gilch, S., et al., "Polyclonal anti-PrP auto-antibodies induced with dimeric PrP interfere efficiently with PrPSc propagation in prion-infected cells", *J. Biol. Chem*. (2003), 278:18524-18531.
Green, J., "Antitumor Effects of Bisphosphonates", *Cancer* Supplement (Feb. 1, 2003), 97(3 Suppl):840-847 (2003).
Griffiths, G., et al., "Liposomally-encapsulated ricin toxoid vaccine delivered intratracheally elicits a good immune response and protects against a lethal pulmonary dose of ricin toxin", *Vaccine* (1997) 15:1933-1939.
Hanan, E., et al., "Immunomodulation of the Human Prion Peptide 106-126 Aggregation", *Biochemical and Biophysical Research Communications* (2001), 280:115-120.
Hanan, E., et al., "Antiaggregating Antibody Raised Against Human PrP 106-126 Recognizes Pathological and Normal Isoforms of the Whole Prion Protein", *Cellular and Molecular Neurobiology* (2001), 21:693-703.
Hedlund, J., et al., "Negligible adjuvant effect for antibody responses and frequent adverse events associated with IL-12 treatment in humans vaccinagted with pneumococcal polysaccharide", *Vaccine* (2002), 20:164-169.
Higgins, D., et al., "MF59 adjuvant enhances the immunogenicity of influenza vaccine in both young and old mice", *Vaccine* (1996), 14(6):478-484.
Higgins, P., et al., "Small molecule CCR2 antagonists" *Chemokine Biology—Basic Research and Clinical Application*, vol. II., pp. 115-123.
Howarth, D., et al., "Langerhans Cell Histiocytosis", *Cancer* (May 15, 1999), 85(10):2278-90.
Hughes, D., et al., "Bisphosphonates Promote Apoptosis in Murine Osteoclasts In Vitro and In Vivo", *Journal of Bone and Mineral Research* (1995), vol. 10, No. 10, pp. 1478-1487.

(56) References Cited

OTHER PUBLICATIONS

Jaganathan, K.S., et al., "Strong systemic and mucosal immune responses to surface-modified PLGA microspheres containing recombinant Hepatitis B antigen administered intranasally", *Vaccine* (2006), 24:4201-4211.
Jakubzick, C., et al., "Blood monocyte subsets differentially give rise to CD103+ and CD103− pulmonary dendritic cell populations", *J Immunol* (2008), 180:3019-3027.
Jakubzick, C., et al., "Optimization of methods to study pulmonary dendritic cell migration reveals distinct capacities of DC subsets to acquire soluble versus particulate antigen". *J Immunol Methods.* (2008), 337(2):121-131.
Jordan, M., et al., "Liposomal clodronate as a novel agent for treating autoimmune hemolytic anemia in a mouse model", *Blood.* (Jan. 15, 2003), 101(2):594-601.
Kende, M., et al., "Enhancement of intranasal vaccination in mice with deglycosylated chain A ricin by LTR72, a novel mucosal adjuvant", *Vaccine* (2006), 24:2213-2221.
Kenney, R., et al., "Protective Immunity Using Recombinannt Human IL-12 and Alum as Adjuvants in a Primate Model of Cutaneous Leishmaniasis", *The Journal of Immunology* (1999), 163:4481-4488.
Koller, M., et al., "Induction of antibodies against murine full-length prion protein in wild-type mice", *Journal of Neuroimmunology* (2002), 132:113-116.
Kusmartsev, S., et al., "Role of immature myeloid cells in mechanisms of immune evasion in cancer", *Cancer Immunol Immunother.* (2006), 55(3):237-245.
Kusmartsev, S., et al., "Reversal of myeloid cell-mediated immunosuppression in patients with metastatic renal cell carcinoma", *Clin Cancer Res* (Dec. 15, 2008), 14(24):8270-8278.
Langermans, J., et al., "Effect of adjuvant on reactogenicity and long-term immunogenicity of the malaria Vaccine ICC-1132 in macaques", *Vaccine* (2005) 23:4935-4943.
Lauren, L., et al., "Pharmacokinetics of Clodronate after Single Intravenous, Intramuscular and Subcutaneous Injections in Rats", *Pharmacology & Toxicology* (1991), vol. 69, 365-368.
Lehenkari, P., et al., "Further Insight into Mechanism of Action of Clodronate: Inhibition of Mitochondrial ADP/ATP Translocase by a Nonhydrolyzable, Adenine-Containing Metabolite", *Mol. Pharmacol.* (2002), 62(2):1255-1262.
Levesque, P., et al., "Association Between Immunogenicity and Adsorption of a Recombinant *Streptococcus pneumoniae* Vaccine Antigen by an Aluminum Adjuvant", *Human Vaccines* (2006), 2(2):74-77.
Lin, J., "Bisphosphonates: A review of Their Pharmacokinetic Properties", *Bone* (Feb. 1996), vol. 18, No. 2, pp. 75-85.
Loike, J., et al., "A Fluorescense Quenching Technique Using Trypan Blue to Differentiate between Attached and Ingested Glutaraldehyde-Fixed Red Blood Cells in Phagocytosing Murine Macrophages", *Journal of Immunological Methods* (1983), 57:373-379.
Mantovani, A., et al., "Macrophages, innate immunity and cancer: balance, tolerance, and diversity", *Current Opinion in Immunology* (2010), 22:231-237.
Mantovani, A., "Molecular pathways linking inflammation and cancer", *Curr. Mol. Med.* (2010), 10(4):369-373.
Martin, J., "Development of an Adjuvant to Enhance the Immune Response to Influenza Vaccine in the Elderly", *Biologicals* (1997), 25:209-213.
Mathes, M., et al., "Evaluation of liposomal clodronate in experimental spontaneous autoimmune hemolytic anemia in dogs", *Experimental Hermatology* (2006), 34:1393-1402.
Mendez, S., et al., "Coinjection with CpG-Containing Immunostimulatory Oligodeoxynucleotides Reduces the Pathogencity of a Live Vaccine against Cutaneous Leishmaniasis but Maintains Its Potency and Durability", *Infection and Immunity*, Sep. 2003, p. 5121-5129.
Mirzadegan, T., et al., "Identification of the binding site for a novel class of CCR2b chemokine receptor antagonists: binding to a common chemokine receptor motif within the helical bundle", *The Journal of Biological Chemistry* (Aug. 18, 2000), 275(33):25562-25571.
Monkkonen, J., et al., "The Effects of Liposome-Encapsulated and Free Clodronate on the Growth of Macrophage-like Cells In Vitro: The Role of Calcium and Iron", *Calcif Tissue Int* (1993), 53(2):139-146.
Monkkonen, J., et al., "Growth Inhibition of Macrophage-Like and Other Cell Types by Liposome-Encapsulated, Calcium-Bound, and Free Bisphosphonates In Vitro", *Journal of Drug Targeting* (1994), vol. 2(4), pp. 299-308.
Moore, K., et al., "Intracellular Infection by *Leishmania donovani* Inhibits Macrophage Apoptosis", *Journal of Immunology* (1994), 152:2930-2937.
Moore, P., et al., "Canine Hemophagocytic Histiocytic Sarcoma: A Proliferative Disorder of CD11d+ Macrophages", *Vet Pathol.* (2006), 43(5):632-645.
Mullen, G., et al., "Enhancement of functional antibody responses to AMA1-C1/Alhydrogel®, a *Plasmodium falciparum* malaria vaccine, with CpG oligodeoxynucleotide", *Vaccine* (2006), 24:2497-2505.
Nakano, H., et al., "Blood-derived inflammatory dendritic cells in lymph nodes stimulate acute T helper type 1 immune responses", *Nature Immunology* (Apr. 2009), 10(4):394-402.
Ostrand-Rosenberg et al., "Antagonists of tumor-specific immunity: tumor-induced immune suppression and host genes that co-opt the anti-tumor immune response", *Breast Disease* (2004), 20:127-135, IOS Press.
Ostrand-Rosenberg et al., "Myeloid-derived suppressor cells: linking inflammation and cancer", *J Immunol* (2009), 182:4499-4506.
Palese, P., "Making Better Influenza Virus Vaccines?", *Emerging Infectious Diseases* (2006), 12(1):61-65.
Peng, M., et al., "Novel vaccines for the treatment of chronic HBV infection based on mycobacterial heat shock protein 70", *Vaccine* (2006), 24:887-896.
Peretz, D., et al., "Antibodies inhibit prion propagation and clear cell cultures of prion infectivity", *Nature* (Aug. 16, 2001), 412:739-743.
Petrik, M., et al., "Aluminum Adjuvant Linked to Gulf War Illness Induces Motor Neuron Death in Mice", *NeuroMolecular Medicine* (2007), 9(1):83-100.
Pimenta, F., et al., "Intranasal Immunization with the Cholera Toxin B Subunit-Pneumococcal Surface Antigen A Fusion Protein Induces Protection against Colonization with *Streptococcus pneumoniae* and Has Negligible Impact on the Nasopharyngeal and Oral Microbiota of Mice", *Infection and Immunity* (Aug. 2006), 74(8):4939-4944.
Pollard, J.W., "Tumour-educated macrophages promote tumour progression and metastasis", *Nature Reviews Cancer* (Jan. 2004), 4:71-78.
Polymenldou, M., et al., "Humoral immune response to native eukaryotic prion protein correlates with anti-prion protection", *Proc. Natl. Acad. Sci.* (Oct. 5, 2004), 101(Suppl. 2):14670-14676.
Qian, Bin-Zhi, et al., "CCL2 recruits inflammatory monocytes to facilitate breast-tumour metastasis", *Nature.* (2011), 475(7355):222-225.
Qin, W., et al., "CpG ODN Enhances Immunization Effects of Hepatitis B Vaccine in Aged Mice", *Cellular & Molecular Immunology* (2004), 1(2):148-152.
Randolph, G.J., et al., "A soluble gradient of endogenous monocyte chemoattractant protein-1 promotes the transendothelial migration of monocytes in vitro", *The Journal of Immunology* (1995), 155:3610-3618.
Randolph, G.J., et al., "Differentiation of phagocytic monocytes into lymph node dendritic cells in vivo", *Immunity* (Dec. 1999), 11:753-761.
Roelofs, A., et al., "Molecular Mechanisms of Action of Bisphosphonates: Current Status", *Clin Cancer Res* (20 Suppl.) (Oct. 15, 2006), 12:6222s-6230.
Rogers, M., et al., "Cellular and Molecular Mechanisms of Action of Bisphosphonates", *Cancer Supplement* (Jun. 15, 2000), 88(12):2961-2978.
Rosado-Vallado, M., et al., "Aluminium phosphate potentiates the efficacy of DNA vaccines against *Leishmania mexicana*", *Vaccine* (2005), 23:5372-5379.

(56) References Cited

OTHER PUBLICATIONS

Rosset, M., et al., "BreakingImmune Tolerance to the Prion Protein Using Prion Protein Peptides Plus Oligodeoxynucleotide-CpG in Mice", *The Journal of Immunology* (2004), 172:5168-5174.
Sabirov, A., et al., "Intranasal vaccination of neonatal mice with polysaccharide conjugate vaccine for protection against pneumococcal otitis media", *Vaccine* (2006), 24:5584-5592.
Schwarz, A., et al., "Immunisation with a synthetic prion protein-derived peptide prolongs survival times of mice orally exposed to the scrapie agent", *Neuroscience Letters* (2003), 350:187-189.
Segura-Velazquez, R., et al., "A novel synthetic adjuvant effectively enhances the immunogenicity of the influenza vaccine", *Vaccine* (2006), 24:1073-1080.
Selander, K., et al., "The Effects of bisphosphonates on the Resorption Cycle of Isolated Osteoclasts", *Calcified Tissue International* (1994), 55:368-375.
Selander, K., et al., "Characteristics of Clodronate-Induced Apoptosis in Osteoclasts and Macrophages", *Molecular Pharmacology* (1996), 50:1127-1138.
Sen, G., et al., "Immunization of Aged Mice with a Pneumococcal Conjugate Vaccine Combined with an Unmethylated CpG-Containing Oligodeoxynucleotide Restores Defective Immunoglobulin G Antipolysaccharide Responses and Specific CD4+-T-Cell Priming to Young Adult Levels", *Infection and Immunity* (2006), 74:2177-2186.
Serafini, P., et al., "Myeloid suppressor cells in cancer: recruitment, phenotype, properties, and mechanisms of immune suppression", *Seminars in Cancer Biology* 2006;16:53-65.
Sica, A., "Role of tumour-associated macrophages in cancer-related inflammation", *Experimental Oncology* (Sep. 2010), 32(3):153-158.
Sigurdsson, E., et al., "Immunization Delays the Onset of Prion Disease in Mice", *American Journal of Pathology* (Jul. 2002), 161(1):13-17.
Skorupski, K., et al., "CCNU for the Treatment of Dogs with Histiocytic Sarcoma", *J Vet Intern Med* (2007), 21:121-126.
Solinas, G., et al., "Inflammation-mediated promotion of invasion and metastasis", *Cancer Metastasis Rev* (2010), 29:243-248.
Souan, L., et al., "Modulation of proteinase-K resistant prion protein by prion peptide immunization", *Eur. J. Immunol.* (2001), 31:2338-2346.
Stewart, V., et al., "Pre-clinical evaluation of new adjuvant formulations to improve the immunogenicity of the malaria vaccine RTS,S/AS02A", *Vaccine* (2006), 24:6483-6492.
Sugai, T., et al., "A CpG-containing oligodeoxynucleotide as an efficient adjuvant counterbalancing the Th1/Th2 immune response in diphtheria-tetanus-pertussis vaccine", *Vaccine* (2005), 23:5450-5456.
Suli, J., et al., "Experimental squaleneadjuvant I. Preparation and testing of its effectiveness", *Vaccine* (2004), 22:3464-3469.
Tacke, F., et al., "Monocyte subsets differentially employ CCR2, CCR5, and CX3CR1 to accumulate within atherosclerotic plaques", *The Journal of Clinical Investigation* (Jan. 2007), 117(1):185-194.
Theeten, H., et al., "Effects of lowering the aluminium content of a dTpa vaccine on its immunogenicity and reactogenicity when given as a booster to adolescents", *Vaccine* (2005), 23:1515-1521.
Twentyman, P.R., et al., "A study of some variables in a tetrazolium dye (MTT) based assay for cell growth and chemosensitivity", *Br. J. Cancer* (1987), 56:279-285.
van Engeland, M., et al., "Annexin V-Affinity Assay: A Review on an Apoptosis Detection System Based on Phosphatidylserine Exposure", *Cytometry* (1998), 31:1-9.
van Rooijen, N., et al., "Effects of Intracellular Diphosphonates on Cells of the Mononuclear Phagocyte System: In Vivo Effects of Liposome-Encapsulated Diphosphonates on Different Macrophage Subpopulations in the Spleen", *Calcif Tissue Int* (1989), 45 (3):153-156.
van Rooijen, N., et al., "In vitro and in vivo elimination of macrophage tumor cells using liposome-encapsulated dichloromethylene diphosphonate", *Virchows Archiv B Cell Pathol* (1988), 54:241-245.
van Rooijen, N., et al., "Liposome mediated depletion of macrophages: mechanism of action, preparation of liposomes and applications", *Journal of Immunological Methods* (1994), 174:83-93.
van Rooijen, N., et al., "Apoptosis of macrophages induced by liposome-mediated intracellular delivery of clodronate and propamidine", *Journal of Immunological Methods* (1996) 193:93-99.
Vermes, I., et al., "A novel assay for apoptosis Flow cytometric detection of phosphatidylserine expression on early apoptotic cells using fluorescein labelled Annexin V", *Journal of Immunological Methods* (1995), 184:39-51.
Villikka, K., et al., "The Absolute Bioavailability of Clodronate From Two Different Oral Doses", *Bone* (Sep. 2002), 31(3):418-421.
Vitetta, E., et al., "A pilot clinical trial of a recombinant ricin vaccine in normal humans", *Proc. Natl. Acad. Sci.* (Feb. 14, 2006) 103(7):2268-2273.
Wellman, M., et al., "A Macrophage-Monocyte Cell Line From a Dog with Malignant Histiocytosis", *In Vitro Cellular & Developmental Biology* (Mar. 1988), vol. 24, No. 3, Part I, pp. 223-229.
Witz IP, "Tumor-microenvironment interactions: dangerous liaisons", *Advances in Cancer Research* (2008), 100:203-229.
Youn, Je-In, et al., "The biology of myeloid-derived suppressor cells: the blessing and the curse of morphological and functional heterogeneity", *Eur J Immunol.* (Nov. 2010), 40(11):2969-2975.
Zavodovskaya, R., et al., "Evaluation of dysregulation of the receptor tyrosine kinases Kit, Flt3, and Met in histiocytic sarcomas of dogs", *J Am Vet Med Assoc* (2006), 67(4):633-641.
Zeisberger, SM, et al., "Clodronate-liposome-mediated depletion of tumour-associated macrophages: a new and highly effective antiangiogenic therapy approach", *British Journal of Cancer* (2006), 95:272-281.
Hughes, R.O. et al., "Discovery of ((1S,3R)-1-isopropyl-3-((3S,4S)-3-methoxy-tetrahydro-2H-pyran-4-ylamino)cyclopentyl)(4-(5-(trifluoromethyl)pyridazin-3-yl)piperazin-1-yl)methanone, PF-4254196, a CCR2 antagonist with an improved cardiovascular profile", Bioorganic & Medicinal Chemistry Letters (2011), 21: 2626-2630.
Lin, K.L. et al., "CCR2-Antagonist Prophylaxis Reduces Pulmonary Immune Pathology and Markedly Improves Survival during Influenza Infection", The Journal of Immunology (2011), 186: 508-515.

* cited by examiner

Regression of lung and pleural metastases in histiocytic sarcoma after LC + chemo

MYELOID DERIVED SUPPRESSOR CELL INHIBITING AGENTS

CROSS REFERENCE TO RELATED APPLICATIONS

The present application is a continuation-in-part application of U.S. patent application Ser. No. 13/050,614 filed Mar. 17, 2011. The present application is a continuing application of PCT/US11/29022, filed Mar. 18, 2011. U.S. patent application Ser. No. 13/050,614 claims priority to U.S. Provisional Patent Application No. 61/315,263, filed Mar. 18, 2010. Reference is also made here to U.S. Provisional Patent Application No. 61/422,984, filed Dec. 14, 2010. Reference is also made here to co-pending application, U.S. application Ser. No. 12/393,612, filed Feb. 26, 2009 (claiming priority to U.S. Provisional Application 61/031,410, filed Feb. 26, 2008), entitled, "Liposomal Delivery of Bisphosphonates". The entire disclosure and contents of the above applications are hereby incorporated by reference

FIELD OF INVENTION

The present invention relates to materials that inhibit and/or eliminate vaccine-induced immunosuppressive macrophages. More particularly, the present invention relates to adjuvant additives that enhance vaccine response through inhibition and/or elimination of vaccine-induced immunosuppressive macrophages. The invention also relates to the field of vaccines and adjuvant additives, as additives for conventional vaccines that improve immune response to a vaccine are provided. The present invention also relates to methods for enhancing immune response to a vaccine.

BACKGROUND OF THE INVENTION

Immunologic adjuvants are added to vaccines to stimulate the immune system's response to the target antigen, but do not in themselves confer immunity. Adjuvants can act in various ways in presenting an antigen to the immune system. Adjuvants can act as a depot for the antigen presenting the antigen over a long period of time, thus maximizing the immune response before the body clears the antigen. Examples of depot type adjuvants are oil emulsions. Adjuvants can also act as an irritant which causes the body to recruit and amplify immune response. A tetanus, diphtheria, and pertussis vaccine, for example, contains minute quantities of toxins produced by each of the target bacteria, but also contains some aluminum hydroxide. Such aluminum salts are common adjuvants in vaccines sold in the United States and have been used in vaccines for over 70 years. The body's immune system develops an antitoxin to the bacteria's toxins, not to the aluminum, but would not respond enough without the help of the aluminum adjuvant.

Although immunological adjuvants have traditionally been viewed as substances that aid the immune response to antigen, adjuvants have also evolved as substances that can aid in stabilizing formulations of antigens, especially for vaccines administered for animal health Vaccine preparations have been observed to demonstrate less than robust immune response in vivo, creating a need for the development of enhanced vaccine preparations. However, the exact mechanisms working to inhibit and/or reduce less than robust response to vaccines in vivo remain under study.

All vaccines induce inflammation and any inflammation that is sustained for more than a few hours will result in recruitment of myeloid cells (monocytes and neutrophils) to the site of vaccination and to the vaccine draining lymph nodes. Certain subpopulations of these cells are also referred to as vaccine elicited myeloid cells (VDSC). These cells are also referred to as myeloid derived suppressor cells (MDSC). In certain contexts, prior reports indicate that these inflammatory cells (especially monocytes) recruited to vaccine-draining lymph nodes may actually augment immune response, though information presented in the present disclosure suggests otherwise.

Clodronate is a bisphosphonate drug that kills osteoclasts and other macrophages via induction of apoptosis. When clodronate is incorporated within liposomes (LC), uptake by phagocytic cells such as macrophages is greatly enhanced, resulting in selective targeting of macrophages for killing.[24, 25, 36] Some studies report that repeated LC administration is capable of depleting both tumor associated macrophages and myeloid suppressor cells.[13, 32, 44]

A need remains in the medical arts for improved vaccine preparations with enhanced ability to provoke robust immune response.

SUMMARY OF THE INVENTION

The present invention, in a general and overall sense, provides a family of adjuvants and vaccine/adjuvant additives, myeloid derived suppressor cell inhibiting agents, found to enhance and/or augment the immunoactivity of a vaccine or cancer/tumor inhibiting treatment. The adjuvants and vaccine/adjuvant additives may be used in combination with virtually any conventional adjuvant and/or vaccine, or as an adjuvant alone, to provide an improved therapeutic preparation as a vaccine, as well as together with any variety of cancer treatment therapies (chemotherapy, radiation, cancer vaccine). Methods and compositions are provided that increase the effectiveness of a vaccine and cancer/tumor treatment in a manner that is independent of the type of vaccine adjuvant included in the preparation.

Adjuvants and Vaccine Adjuvant Additives/MDSC Inhibiting Agents and Improved Vaccine Preparations:

In one aspect, the adjuvants and vaccine adjuvant additives described here comprise myeloid derived suppressor cell (MDSC) inhibiting and/or blocking agents. By way of example, suitable drugs to block the suppressive effects of MDSC include tyrosine kinase inhibitors (eg, sunitinib), MDSC differentiating agents (eg, all-trans retinoic acid), reactive nitrogen inhibitors (eg, aminoguanidine or similar drugs); arginase enzyme inhibitors, indoleamine deoxygenase enzyme inhibitors, reactive oxygen species inhibitors, TGF-b inhibitors, IL-10 inhibitors, VEGF inhibitors, and PGE2 synthesis inhibitors.

In some embodiments, the myeloid derived suppressor cell inhibiting agents may be further described as comprising a bisphosphonate drug, such as clodronate, zoledronate, pamidronate, etidronate, or any other type of drug that is capable of depleting or inhibiting macrophages, and that when provided with an adjuvant containing vaccine, provides for an enhanced immune response in an animal greater than the observed immune response in the animal given the adjuvant vaccine preparation without the myeloid derived suppressor cell inhibiting agent. In some embodiments, the bisphosphonate drug is a liposomal conjugated agent, such as liposomal clodronate.

Additional examples of suitable vaccine/adjuvant additives (e.g., MDSC depleting agents) of the invention include liposome-encapsulated bisphosphonate drugs, antibodies targeted to MDSC, liposomes encapsulating other apoptosis inducing agents, or liposomes encapsulating siRNA or other RNA targeting molecules that induce MDSC apoptosis. By way of further example, the vaccine additive of the invention may comprise virtually any agent demonstrated to deplete and/or inhibit the migration, accumulation or activity of myeloid derived suppressor cells (MDSC), thus providing for an inhibition of the immunosuppressive activity of the MDSCs. Additional vaccine additives (MDSC depleting agents) include drugs that block monocyte release from bone marrow (CCL2 or CCR2 inhibitors, competitors or agonists, M-CSF inhibitors, GM-CSF inhibitors). In other embodiments, the adjuvant additives consist of drugs that inhibit the recruitment and/or migration of MDSC to sites of vaccine inflammation. These drugs would consist most specifically of small molecule inhibitors of the receptor for CCL2 (MCP-1), which is known as CCR2. These CCR2 receptor inhibitors block the egress of monocytes from the bone marrow into the bloodstream, and also inhibit the accumulation of monocytes at sites of vaccine-induced inflammation, such as vaccine-draining lymph nodes or the skin site of vaccination. Specific inhibitors in this family include RS102895 (Sigma-Aldrich) and other similar molecules.

Other similar drugs would include other small molecule chemokine/cytokine inhibitors, such as inhibitors of M-CSF, GM-CSF, IL-3, or IL-8, or receptors for these cytokines and chemokines. Other candidates for inhibition would include the S100 family of proteins, including especially S100A8/A9.

The MDSC depleting/inhibiting agents of the invention may be administered orally, i.v., s.c., i.m., or i.p. at the time of vaccination, before the time of vaccination, after the time of vaccination, or before, at the same time and after vaccination.

Methods of Vaccination with MDSC Inhibiting Agents/Vaccine Additive Enhancing Agents:

In another aspect, improved methods of vaccinating an animal are provided. Surprisingly, the present inventors found that the inhibition of a particular population of myeloid derived suppressor cells (the suppressive population of myeloid derived suppressor cells) from moving to the site of vaccination and/or lymph nodes resulted in a demonstrable increase in immune response (resulting in an observable increase in antibody titer in vivo production) in the treated animal. A vast improvement in vivo for inducing a significant and robust immune response was observed. Despite prior teaching that inflammatory monocytes recruited to vaccine-draining lymph nodes may actually augment immune response, the present data and inventive preparations and methods demonstrates the opposite is in fact the case. Inhibiting the recruitment of inflammatory monocytes is suggested by the present data to augment immune response.

In some embodiments, the method comprises administering the vaccine adjuvant additive (e.g., the myeloid derived suppressor cell (MDSC) depleting agent) before, at the same time or slightly after (1 day, 2, days, 3 days, immediately after, several hours after) the time that a vaccine is administered. While not wanting to be limited to any particular mechanism of action, it is proposed that the administration of the vaccine additive at the same time or after the vaccine acts to deplete and/or inhibit the influx of myeloid cells (monocytes and neutrophils) to the site of inflammation (typically the site of vaccination), and to vaccine draining lymph nodes in vivo. The possible routes of drug administration include oral, i.v., s.c., i.m., i.p. or topical at the site of vaccination. Other preferable routes of drug administration would be to mix the adjuvant additive with the vaccine itself, and provide the preparation administered together to an animal.

In some embodiments, the combined vaccination and administration of the myeloid derived suppressor cell inhibiting agent (myeloid cell depletion approach) is repeated each time the vaccine is administered.

The presently described vaccine additives are provided together with a vaccine that includes an adjuvant. Alternatively, the additive may be provided whenever a conventional supplied to an animal, either after or at the same time adjuvant is. By way of example, conventional adjuvants include alum, other compounds of aluminum, *Bacillus* of Calmette and Guerin (BCG), TiterMax® adjuvant, Ribi®, Freund's Complete Adjuvant (FCA) and a new adjuvant disclosed by the United States Department of Agriculture's (USDA) National Wildlife Research Center on their web site at aphis.usda.gov/ws/nwrc/pzp.htm based on Johne's antigen. Alum is generally considered to be any salt of aluminum, in particular, the salts of inorganic acids. Hydroxide and phosphate salts are particularly useful as adjuvants. A suitable alum adjuvant is sold under the trade name, Imject® Alum (Pierce Chemical Company) that consists of an aqueous solution of aluminum hydroxide (45 mg/ml) and magnesium hydroxide (40 mg/ml) plus inactive stabilizers. Alum is a particularly advantageous adjuvant since it already has regulatory approval and it is widely accepted in the art.

The amount of vaccine and/or adjuvant additive to be used depends on the amount and type of the particular antigen used, and on the type of additional adjuvant that may be included with the vaccine, as well as any other treatment being provided along with the vaccine. One skilled in the art can readily determine the amount of vaccine additive needed in a particular application by assessing antibody titer levels and performing a standard dose response curve.

The vaccine regimen of the present invention may include any variety of vaccine antigen, such as a recombinant protein/peptide, a live vector vaccine, killed organism, or cell vaccine. In this regard, the present myeloid derived suppressor cell agents maybe employed as part of a regimen for cancer as well as infectious disease immunization.

Vaccines for Use as Part of the Vaccine Treatment Regimen

It is anticipated that the vaccine regimen of the present invention may include any variety of different antigens, such as recombinant protein/peptides, live vector antigens, killed organism, or cell vaccine. By way of example, the vaccines with which the present additives may be provided include 1.) any infectious agent (bacterial, viral, fungal, protozoal); 2.) vaccines for allergy, 3.) vaccines for autoimmune disorders; 4.) vaccines for toxins; 5.) vaccines for addictive substances (eg., nicotine, alcohol, caffeine, etc.).

The vaccine additives/adjuvant agents may be administered i.p., i.v., mucosally, orally, s.c., or i.m. by injection, together with a conventional vaccine to boost immune response. Examples of conventional adjuvants that may be included with the vaccine as part of the herein described vaccination regimen include alum, or whole killed organism or cell vaccine plus adjuvant, or replicating or non-replicating viral vectored or bacterial vectored vaccines.

The vaccine treatment regimen of the invention provides for the administration of the adjuvant/vaccine additive agent (the myeloid derived suppressor cell inhibiting agent) provided just before, at the same time, just after a conventional vaccine, or before, at the same time and after the conventional vaccine is provided to an animal. The myeloid derived suppressor cell inhibiting agent may be admixed with the vaccine, given adjacent to the vaccine, or given systemically to an animal in order to boost vaccine immune response.

In other embodiments, the vaccine regimen (boosting system) may be administered with cancer vaccines, infectious disease vaccines, with toxoid vaccines, or vaccines against autoimmune antigens. In another aspect, a method for inhibiting tumor growth is provided, such as for inhibiting histiocytic sarcoma and other cancers. An enhanced anti-cancer vaccine treatment preparation that incorporates the myeloid derived suppressor cell agents of the invention is this also provided.

BRIEF DESCRIPTION OF DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein.

DETAILED DESCRIPTION OF THE INVENTION

Figure 1:
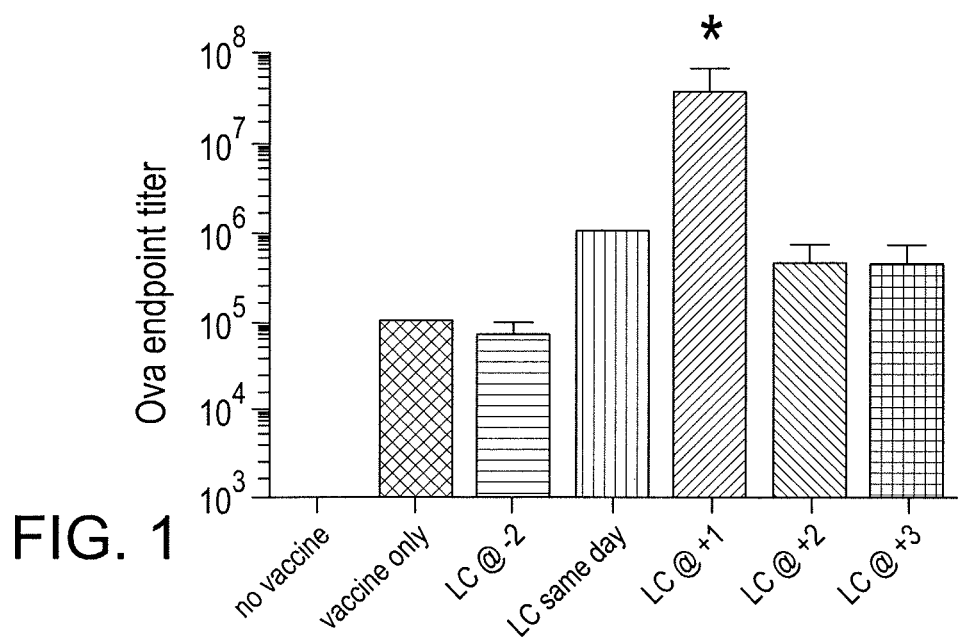
FIG. 1. Effects of liposomal clodronate (LC) administration on antibody responses following vaccination.
Figure 2:
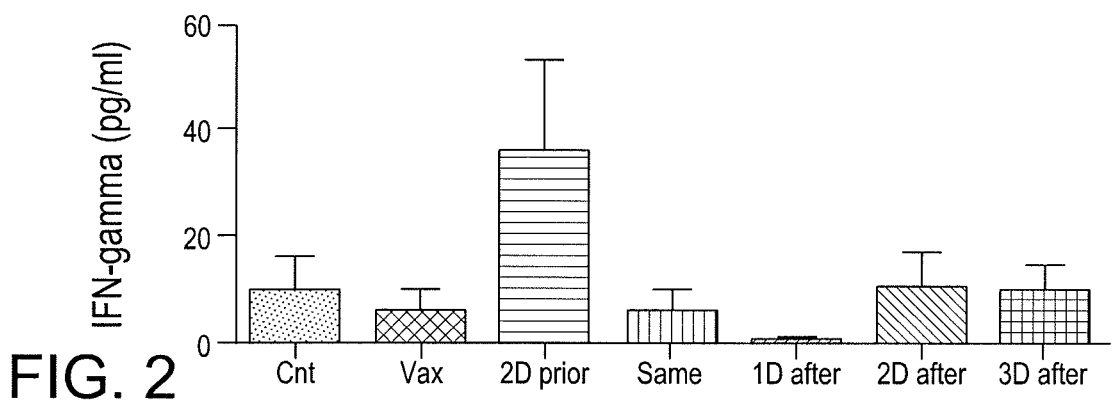
FIG. 2. Effects of liposomal clodronate administration on IFN-g responses by spleen cells from vaccinated mice.

The present invention embraces a unique class of agents described herein as inhibitory myeloid derived suppressor cell (MDSC) agents that are useful in enhancing immune response to adjuvinated vaccine preparations. As part of a vaccine regimen, the MDSI agents of the invention may be included with any variety of vaccines, such as recombinant, live vectored, killed organism, or cell vaccine. It is also envisioned that the present MDSI agents may be provided with cancer and infectious disease treatment methods to enhance the effectiveness of these treatment methods (anto-tumor, anti-viral, etc., effectiveness).

By way of further example, the vaccine with which the present MDSI agents may be included to enhance effectiveness include vaccines for: 1.) any infectious agent (bacterial, viral, fungal, protozoal); 2.) vaccines for allergy, 3.) vaccines for autoimmune disorders; 4.) vaccines for toxins; 5.) vaccines for addictive substances (eg., nicotine, alcohol, caffeine, etc.).

The composition or compositions described herein, may be administered either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration, and are well known to an individual having ordinary skill in this art.

The compositions described herein may be administered independently one or more times to achieve, maintain or improve upon a therapeutic effect. It is well within the skill of an artisan in the pharmacological or medical arts to determine dosage, or whether a suitable dosage of the composition(s) described herein should optionally comprise a single administered dose or multiple administered doses. An appropriate dosage depends on the subject's health, the elicitation of the immune responses and/or treatment of the cancer or pathogen associated disease, the route of administration and the formulation used, among other factors.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein.

DEFINITIONS

The term "comprising" means "including" as well as "consisting" e.g. a composition "comprising" X may consist exclusively of X or may include something additional e.g. X+Y.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "adjuvant" has its conventional meaning, i.e., the ability to enhance the immune response to a particular antigen. Such ability is manifested by a significant increase in immune-mediated protection. An enhancement of Immoral immunity is typically manifested by a significant increase (usually >10%) in the titer of antibody raised to the antigen. Similarly, enhancement of cellular immunity is typically manifested by a significant increase (usually >10%) in the number of responding CD8+ or CD4+ T cells. The term "about" in relation to a numerical value x means, for example, x.+−.10%.

As used here, the term "myeloid derived suppressor cell inhibiting agent" may be described as an agent that is capable of inhibiting inflammation induced activity (migration, accumulation, other activity) of a population of myeloid cells recognized as myeloid derived suppressor cells.

The term "antibody" is used in the broadest sense, and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnounal vascular proliferation associated with phakomatoses, edema (such as that associated with brain tumors), and Meigs' syndrome.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is believed to be a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

By "micrometastasis" is meant a small number of cells that have spread from the primary tumor to other parts of the body. Micrometastasis may or may not be detected in a screening or diagnostic test.

"Cancer recurrence" herein refers to a return of cancer following treatment, and includes return of cancer in the primary organ, as well as distant recurrence, where the cancer returns outside of the primary organ.

A subject at "high risk of cancer recurrence" is one who has a greater chance of experiencing recurrence of cancer. For example, relatively young subjects (e.g., less than about 50 years old), those with positive lymph nodes, particularly 4 or more involved lymph nodes (including 4-9 involved lymph nodes, and 10 or more involved lymph nodes), and those with tumors greater than 2 cm in diameter, e.g., in breast cancer patients. A subject's risk level can be determined by a skilled physician. Generally, such high risk subjects will have lymph node involvement (for example with 4 or more involved lymph nodes); however, subjects without lymph node involvement are also high risk, for example if their tumor is greater or equal to 2 cm.

"Decrease in risk of cancer recurrence" is meant reducing the likelihood of experiencing recurrence of cancer relative to an untreated patient (i.e., relative to a patient not treated with a regimen that includes the MDSC inhibiting agent), or relative to a control treatment protocol, such as treatment only with the chemotherapeutic agent, such as those used in the standard of care for colorectal cancer, e.g., leucovorin, 5-fluorouracil, oxaliplatin, irinotecan or a combination thereof. Cancer recurrence is monitored for at least about two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

"Initiation of treatment" refers to the start of a treatment regimen following surgical removal of a tumor. In one embodiment, such may refer to administration of one or more chemotherapeutic agents following surgery. Alternatively, this can refer to an initial administration of a treatment that includes the MDSC inhibiting agent and one or more chemotherapeutic agent.

By "curing" cancer is herein is meant the absence of cancer recurrence at about 2, 3, 4 or about 5 years after beginning adjuvant therapy, depending on the type of cancer.

"Tumor", as used herein, refers to all neoplastic cell growth and proliferation, whether malignant or benign, and all pre-cancerous and cancerous cells and tissues.

The term "anti-cancer therapy" refers to a therapy useful in treating cancer. Examples of anti-cancer therapeutic agents include, but are limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, TRAIL/Apo2, and other bioactive and organic chemical agents, etc. Combinations of two or more of these agents are also included in the invention.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone), a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1$^3$ dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases or micrometastases, the size of the primary tumor or the presence or the size of the dormant tumor.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

The term "therapeutically effective amount" refers to an amount of a compound, preparation or regimen effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. For the treatment of tumor dormancy or micrometastases, the therapeutically effective amount of the drug may reduce the number or proliferation of micrometastases; reduce or prevent the growth of a dormant tumor; or reduce or prevent the recurrence of a tumor after treatment or removal (e.g., using an anti-cancer therapy such as surgery, radiation therapy, or chemotherapy). To the extent the drug may prevent growth and/or kill existing cancer cells, it may be cytostatic and/or cytotoxic. For cancer therapy, efficacy in vivo can, for example, be measured by assessing the duration of survival, disease free survival (DFS), time to disease progression (TTP), duration of progression free survival (PFS), the response rates (RR), duration of response, time in remission, and/or quality of life. The effective amount may improve disease free survival (DFS), improve overall survival (OS), decrease likelihood of recurrence, extend time to recurrence, extend time to distant recurrence (i.e., recurrence outside of the primary site), cure cancer, improve symptoms of cancer (e.g., as gauged using a cancer specific survey), reduce appearance of second primary cancer, etc.

"Treatment" refers to both therapeutic treatment and prophylactic or preventative measures. Those in need of treatment include those already with the disorder as well as those in which the disorder is to be prevented, including those in which the occurrence or recurrence of cancer is to be prevented.

The following examples are presented to illustrate certain embodiments of the invention.

Example 1

Effects of Liposomal Clodronate (LC) Administration on Antibody Responses and IFN Following Vaccination The present example is provided to demonstrate the enhanced antibody response and IFN-γ of an animal to a vaccine containing a conventional adjuvant in conjunction with the MDSC inhibitory additive described herein.

Mice (n=3 per group) were immunized s.c. with 10 ug ovalbumin in a commercial adjuvant (CLDC). At the indicated time points, the mice were also administered liposomal clodronate (LC) an MDSC inhibitory additive, in order to assess the effects of LC administration on conventional vaccine responses. Antibody responses in serum were assessed after 2 rounds of treatment had been administered and anti-ova titers were determined by ELISA.

As demonstrated in FIG. 1, antibody titers in animal given vaccine alone resulted in an ova endpoint titer level of about $10^{(5)}$. The administration of the MDSC inhibitor, LC, 2 days after administration of the Ova vaccine did not appreciably change this antibody titer. However, LC administered on the same day as the vaccine resulted in a measurable increase of antibody titer of about $10^{(6)}$. Even more significantly, LC administration 1 day before administration of the vaccine resulted in a measurable antibody titer level of over $10^{(7)}$. The antibody titer in animals administered the LC vaccine additive 2 days prior to the vaccine was about $10^{(6)}$, with the antibody title in animals administered the LC additive 3 days prior to the vaccine also being about $10^{(6)}$.

Mice were vaccinated with Ova, with or without the administration of LC, as described in as described above. After two treatments, the mice were euthanized and the spleen cells were collected and restimulated in vitro with Ova and 18 hours later, culture supernatants were analyzed for release of IFN-γ. Pre-treatment of mice by one day with LC resulted in a significant increase in IFN-γ production in lymphocytes of vaccinated mice response to Ova restimulation.

The present results demonstrate the enhanced immune response in increased antibody titer levels and IFN-γ, provided upon administration fo the MDSC inhibiting agents, such as LC, with a vaccine preparation containing an adjuvant.

Example 2

Co-Administration of LC with a Vaccine Results in Elimination of Gr-1+ Myeloid Derived Suppressor Cells (MDSC) in Draining Lymph Nodes The present example demonstrates that the use of the vaccine additive (such as LC) together with a vaccine will block and/or eliminate the presence of myeloid derived suppressor cells (MDSC) in draining lymph nodes in vivo. Removing the vaccine-inhibiting activity of the MDSCs to provide a more robust immune response to the vaccine. More specifically, the present example demonstrates the effects of liposomal clodronate (LC) on the immunosuppressive MDSC population of cells, which are elicited by the vaccine and typically accumulate in draining lymph nodes. In addition, the elimination of interference with the recruitment of monocytic and/or neutrophilic MDSC to tumor and lymph node tissues in response to tumor derived chemokines is demonstrated when the vaccine additive (MDSC inhibiting agent) is administered along with a vaccine.

Mice (n=3 per group) were immunized with vaccine alone (Vax alone), LC alone, or with LC plus the vaccine (Vax+LC) and the draining lymph nodes were collected 48 h later and the cells in the lymph nodes were analyzed by flow cytometry to determine the number of Gr-1+ MSC.

Figure 3:
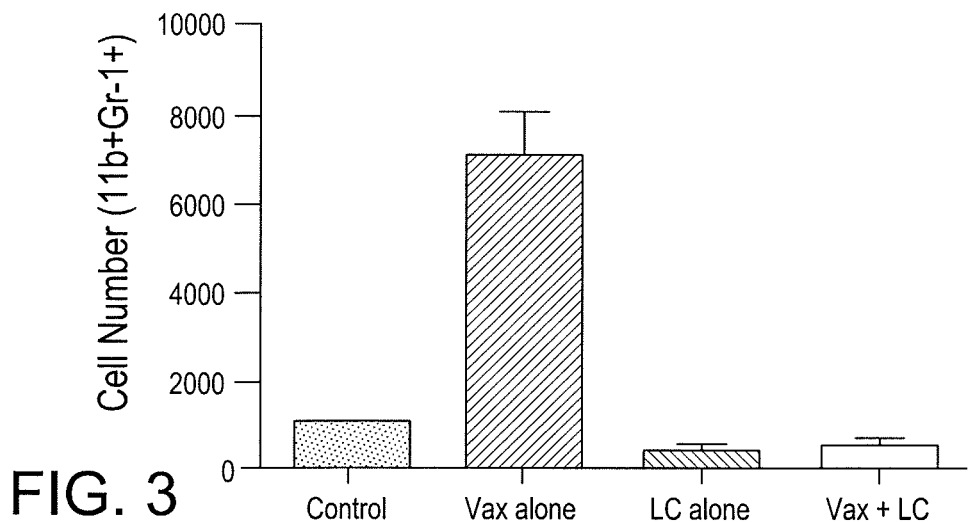
FIG. 3. Co-administration of LC with a vaccine results in elimination of Gr-1+ myeloid suppressor cells (MSC) in draining lymph nodes.

As demonstrated in the data presented at FIG. 3, when mice were vaccinated alone, there was a large increase in the number of MDSC (7,000+/−50 Cells). However, when the mice were co-vaccinated with a conventional vaccine together with LC (Vax+LC), the numbers of MDSC that accumulated in the draining lymph node were significantly suppressed (500+/−10 Cells), by at least 14-fold, compared to administration of vaccine without LC.

Example 3

Depletion of Immunosuppressive Myeloid Derived Suppressor Cells Generates Tumor Immunity and Elicits Antitumor Activite In Vivo The present example demonstrates the utility of the present invention for providing an enhancement of vaccine activity in tumor bearing animals. In addition, the present example demonstrates the utility of the present vaccine adjuvant additives (MCSC inhibiting agents) for reducing tumor growth in vivo. In addition, the present example demonstrates the utility of the invention for providing an enhanced vaccine preparation for tumor bearing animals through depletion of suppressive myeloid derived cells.

Two populations of myeloid cells with opposing functions are generated in response to inflammation. These two different subsets of MDSCs suppress immunity via different mechanisms. The balance between these two populations regulates innate and adaptive immunity in an animal. The present inventors have found that removing the suppressive population of myeloid derived suppressor cells that are stimulated during inflammation has a marked impact on new and adaptive immune responses in vivo.

It has been reported that immature myeloid cells generated by inflammation suppresses immune responses.

Figure 4:
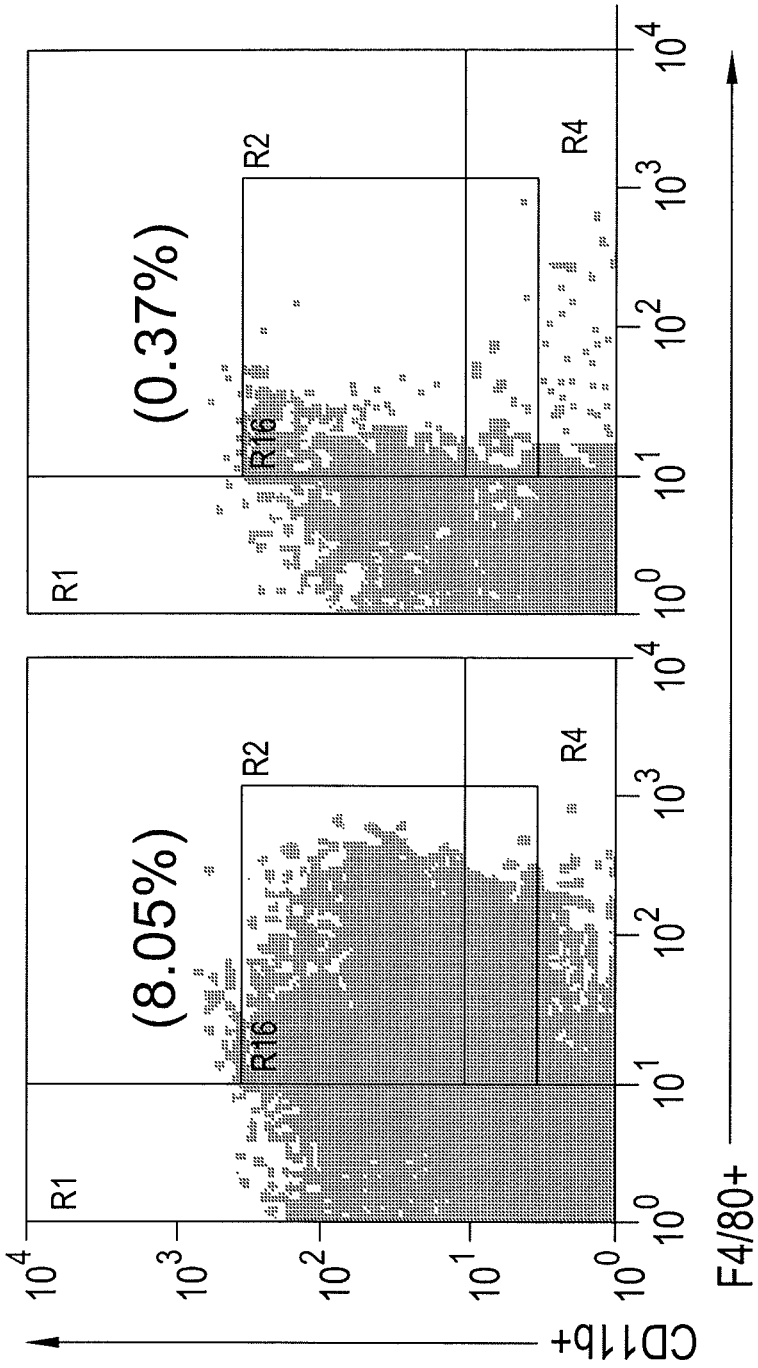
FIG. 4. Efficient systemic depletion of phagocytic cells following LC injection.

FIG. 4 demonstrates that injection of LC, and MDSC suppressing agent, results in the efficient and systemic depletion of phagocyte cells. As shown in FIG. 4A, before treatment demonstrated a population of macrophages of 8.05% of total spleen cells, while administration of LC after 24 hours resulted in a marked reduction in splenic macrophages to only 0.37% of the total cells.

Figure 5:
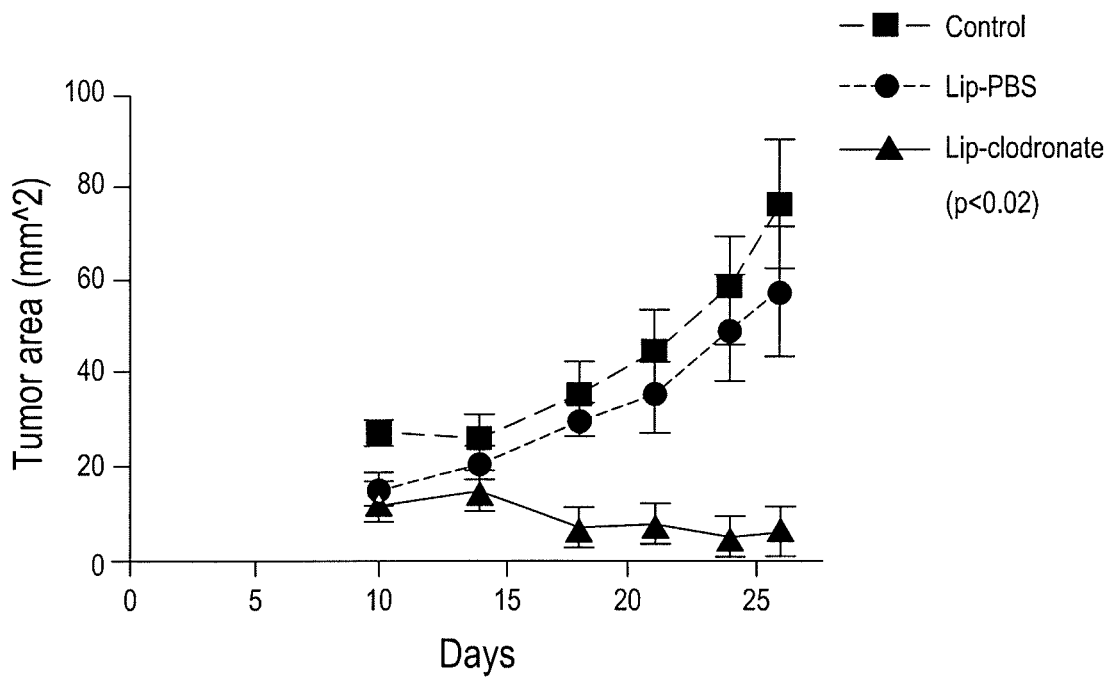
FIG. 5. LC Treatment elicits potent antitumor activity in mouse tumor models (square=Control; circle=Lip-PBS; triangle=Lip-chloronate (p<0.02).

FIG. 5 demonstrates the effect of depleting phagocytic myeloid cells in mice with established syngeneic tumors. Administration of liposomal clodronate (LC) (-▲-) significantly reduced tumor area size at 15 days post treatement (tumor area less than 10 mm$^2$ at about 18 days), while tumor area continued to increase in mice treated with liposomes with phosphate bufered saline (tumor area 30 mm$^2$ at about 18 days) (Lip-PBS) (-●-), similar to the continued tumor area growth seen in non-treated Control mice with tumors (-■-).

Figure 6:
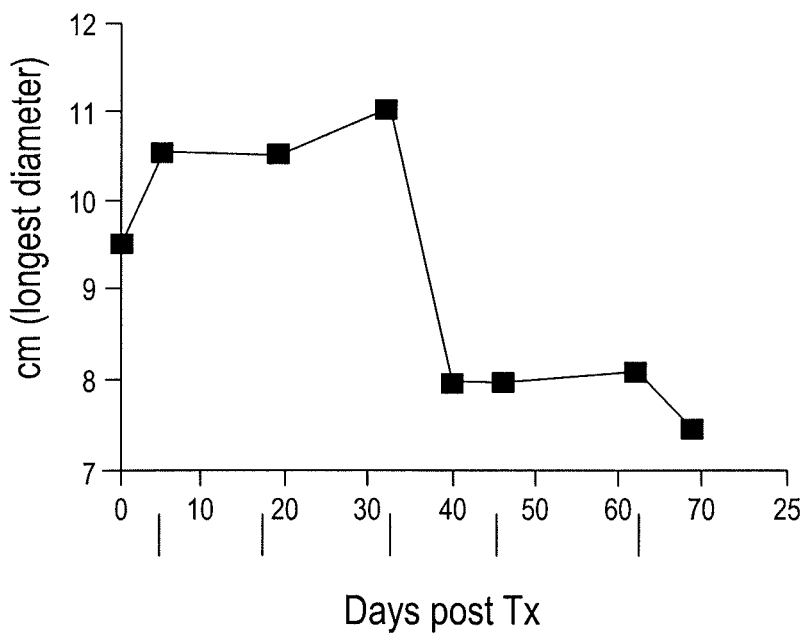
FIG. 6. Tumor regression in dogs with soft tissue sarcoma following LC treatment.

FIG. 6 demonstrates a marked regression of tumor size in dogs with soft tissue sarcoma following LC treatment. Soft tissue sarcoma is locally invasive, with surgery being the primary treatment. These sarcomas are also typically chemoresistant.

Dogs having this spontaneous form of soft tissue sarcoma given the LC treatment demonstrated a significant decrease in tumor size at about 40 days post treatment (tumor size pretreatment of about 9.5 cm, tumor size 40 days post LC treatment about 8 cm) (See FIG. 6). These dogs were not vaccinated.

Figure 7:
FIG. 7. Regression of lung and pleural metastases in histiocytic sarcoma after LC+ chemo.
Figure 7:
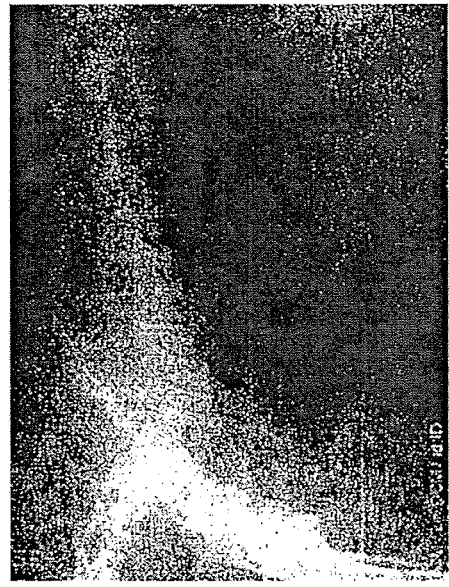
Figure 14:
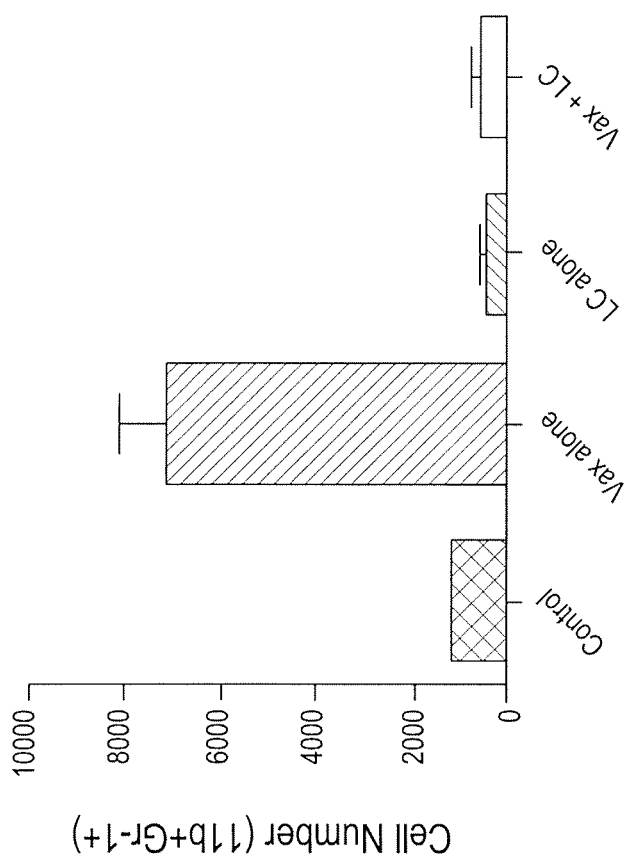
FIG. 14 Co-administration of LC depletes vaccine-induced myeloid cell accumulation in vaccine-draining lymph nodes.

FIG. 7 demonstrates the marked regression of lung and pleural metastasis in histiocytic sarcoma after LC and chemotheraphy treatment (lomustine). Histiocytic sarcomas are very aggressive locally and rapidly metastatic, and chemotheraphy resistant. FIG. 7 (top panel, "Before LC Treatment"), shows significant metastasis of the sarcoma (see heavily occluded image of lung tissue from sarcoma cancer cell proliferation and metastasis), while treatment with LC resulted in almost complete ablation of the occluded lung area after 14 days post treatment (See FIG. 14, Bottom Panel, "Day 14 After Treatment"). These dogs were not vaccinated.

Figure 8:
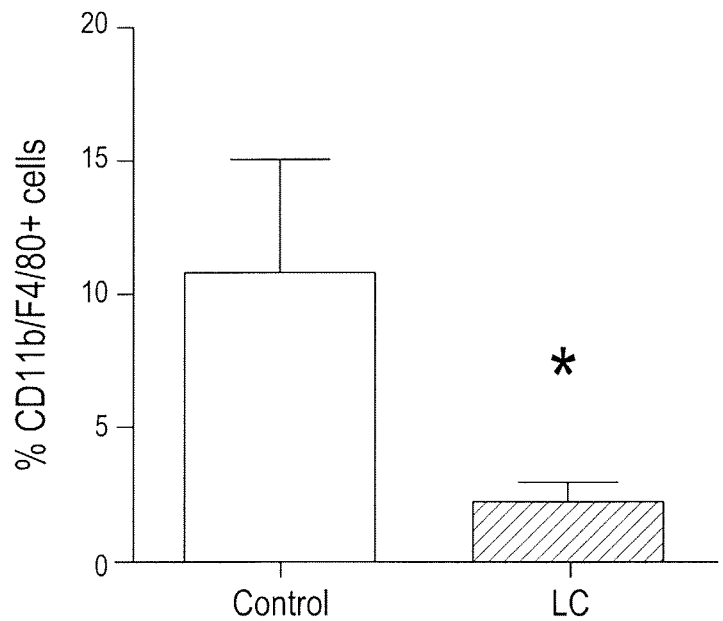
FIG. 8. LC depletes tumor-associated macrophages and myeloid cells.

FIG. 8 demonstrates that administration of the MDSC depleting agent (LC) mediates effects locally in a tumor bearing animal by significantly depleting tumor associated macrophages (Control 11+/−4% CD 11b/F4/80+ cells, LC 2.5+/−1% CD 11b/F4/80+ cells).

Figure 9:
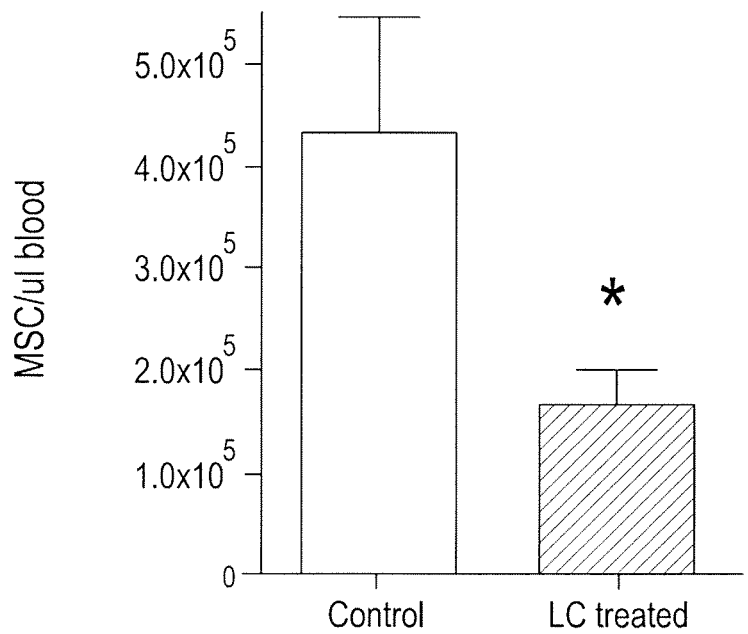
FIG. 9. LC also depletes MDSC in multiple tissue sites.

FIG. 9 demonstrates that administration of the MDSC depleting agent (LC) is also capable of depleting the MDSC population of cells systemically, as it evidenced by suppression in multiple sites. The MSC/ul blood in Control (non-treated animals) was about $4.1 \times 10^5$, while MSC in blood rom LC-treated animal was about $1.9 \times 10^5$.

Figure 10:
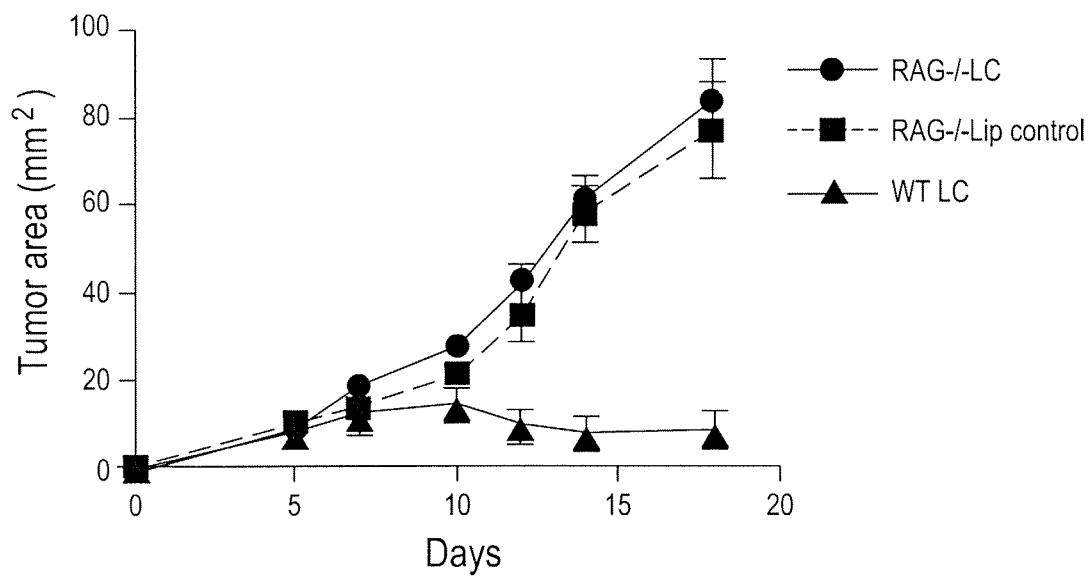
FIG. 10. Antitumor activity elicited by LC treatment is T cell dependent.

FIG. 10 demonstrates that the anititumor activity elicited by LC treatment is T cell dependent (RAG-/-LC=-●-; RAG-/-Lip (Control)=-■-; WT LC=-▲-).

Figure 11:
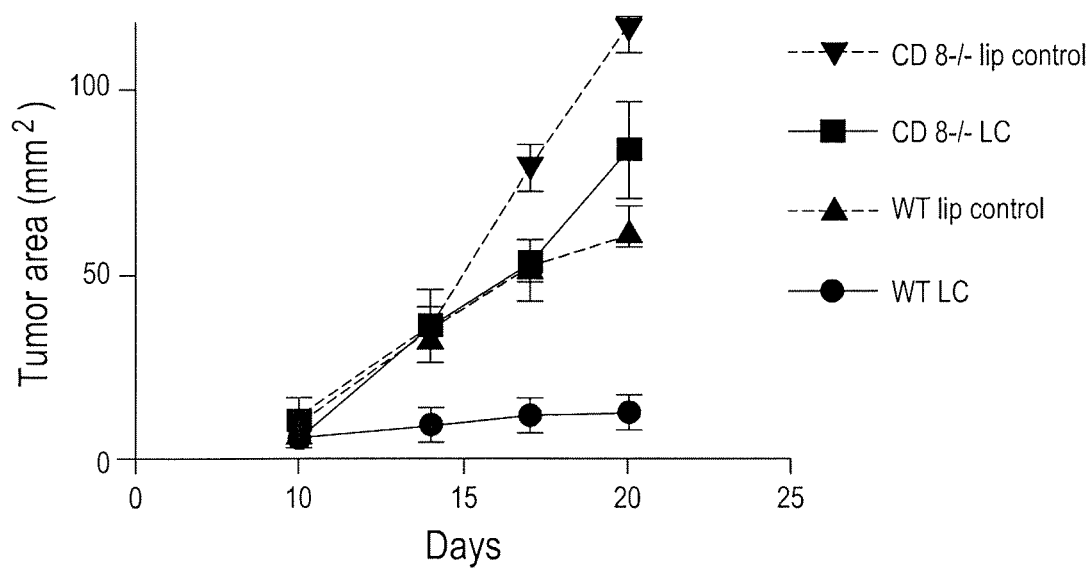
FIG. 11. CD8 T cells are required for LC-induced antitumor activity.

(RAG-/- is recombinase activating gene knockout mouse; WT is wild Type) FIG. 11 demonstrates CD8 cells are required for LC induced antitumor activity. The tumor area in animals treated with WT LC (-●-) remained relatively unchaged up to 20 days after treatment (about 10 mm$^2$), while tumor area significantly increased in animals from the CD 8-/- lip Control group (-▼-) (about 110 mm$^2$ tumor area after 20 days), CD 8-/-LC (-■-) (about 75 mm$^2$ tumor area after 20 days), and WT lip Control group (circle) (about 60 mm$^2$ tumor area after 20 days).

Figure 12:
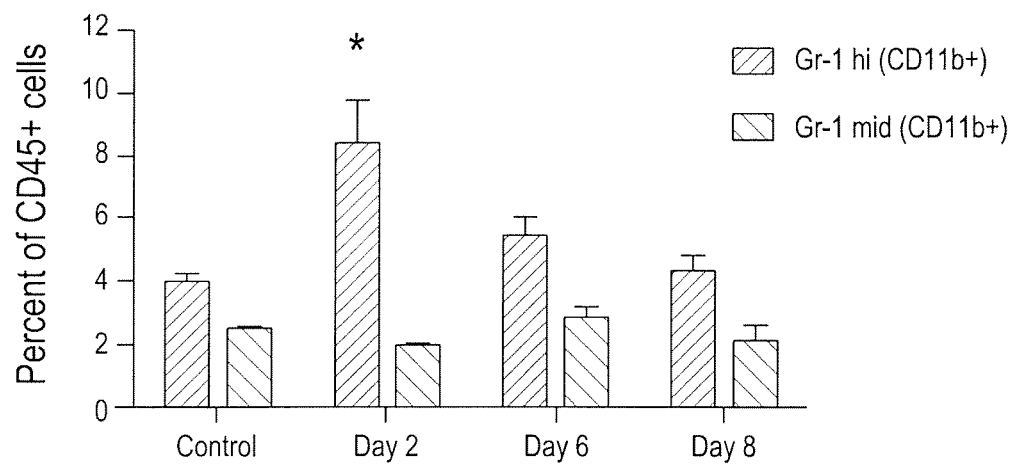
FIG. 12. Rapid kinetics of MDSC expansion following vaccination.

FIG. 12 illustrates the rapid kinetics of MDSC expansion in vivo (Control Gr-1 hi vs Gr-1 mid, Day 2, day 6, Day 8). This data speaks to the mechanism by which it is believed that the vaccine recruits MDSC to the lymph nodes, namely via the bloodstream. So, while not intending to be limited to any specific mechanism of action or to climate consideration of other physiological or other factors, the MDSC depleting agents that work are acting to deplete the MDSC in the bloodstream before they get to the draining lymph nodes.

Figure 13:
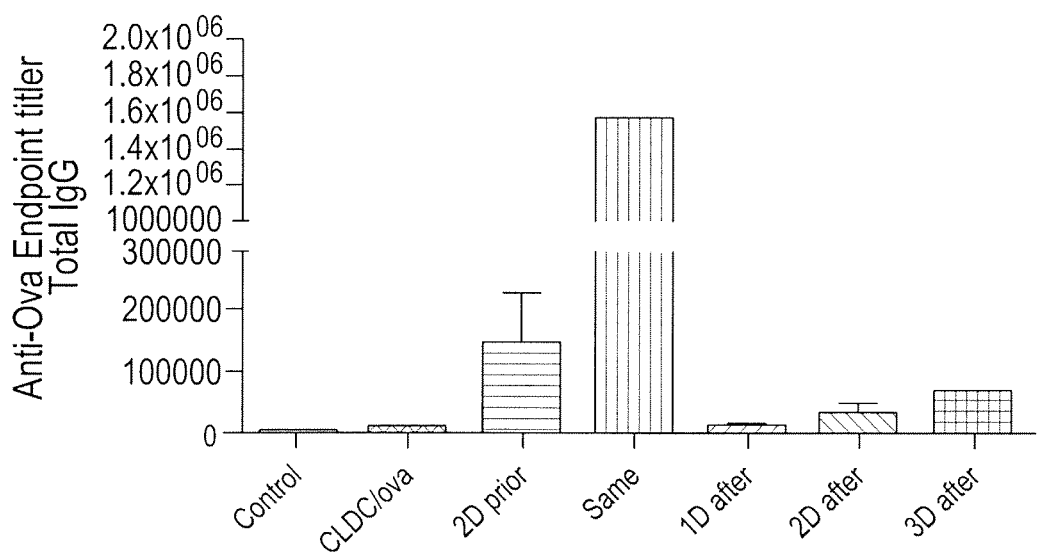

FIG. 13 demonstrates that the concurrent depletion of myeloid cells (by administration of an MDSC depleting agent like LC) at the time of vaccination significantly enhances vaccine responses. The data shows that LC treatment 2 days prior to administration of the Ova vaccine resulted in a significant enhancement of antibody titer, compared to mice that received the vaccine only. However, the greatest enhancement in antibody response occurred when LC was administered on the same day as the vaccine, or one or two days afterwards.

Example 4

CoAdministration of Liposomal Bisphoshonates Depletes Vaccine-Induced MSC Accumulation/Novel Vaccine Adjuvants/Vaccine Additives The present example is provided to demonstrate the utility of the invention as a vaccine additive, and demonstrates the utility of suppressing myeloid suppressor cells as a method for enhancing the vaccine activity and effectiveness in a healthy individual.

In this study, accumulation of MDSC cells in the lymph nodes of control animals and in animals treated with an MDSC depleting agent, LC, was measured. As demonstrated in FIG. 14, the number of cells (11b+Gr-1+) in the control animals was about 1000 (no vaccine, no LC). The number of cells in animals treated with the vaccine alone was about 7.500+/−500. The animals treated with the MDSC depleting agent (LC) alone, demonstrated a cell number of only about 2,500, with a similar number of cells being observed in animals receiving vaccine plus the MDSC depleting agent (LC). This data demonstrates that administration of an MDSC depleting agent will prevent MDSC accumulation in lymph nodes, thus eliminating the "block" typically resulting during a robust immune vaccine response.

Figure 15:
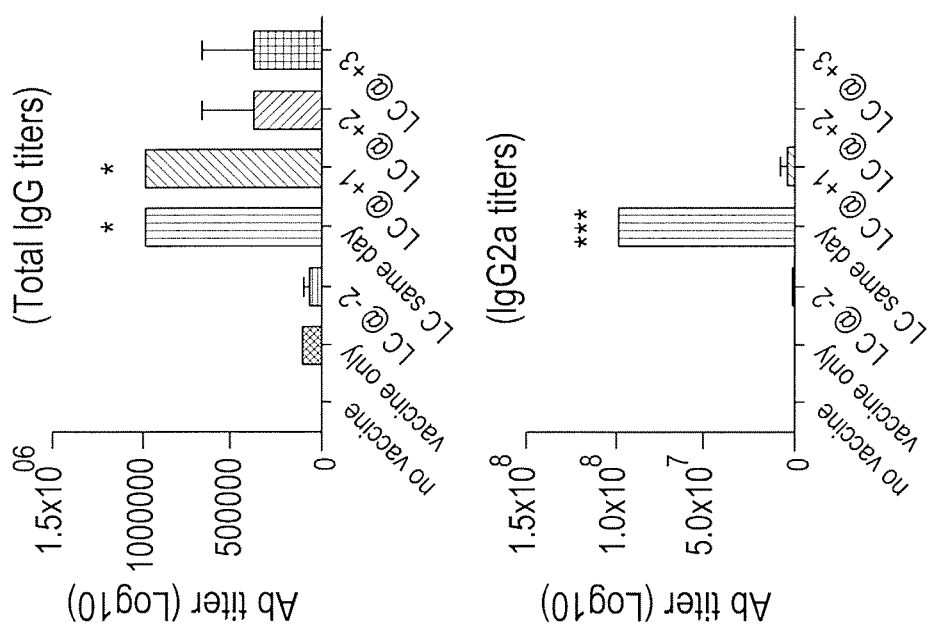
FIG. 15. Co-administration of LC with a conventional vaccine markedly alters vaccine responses.

FIG. 15 demonstrates that total IgG titers in animals treated with a vaccine is significanly enhanced in the presence of an MDSC inhibiting agent, such as LC. The enhancement of IgG titer levels in animals treated with MDSC inhibitng agent (LC) on the same day or 1 day after the vaccine treatment was increased 10-fold over control or vaccine only recieving animals. The IgG titer levels were increased about 5-fold in animals treated with an MDSC inhibiting agent (LC) either 2 days or 3 days after vaccine treatment, compared to controls and vaccine only treated animals.

Figure 16A:
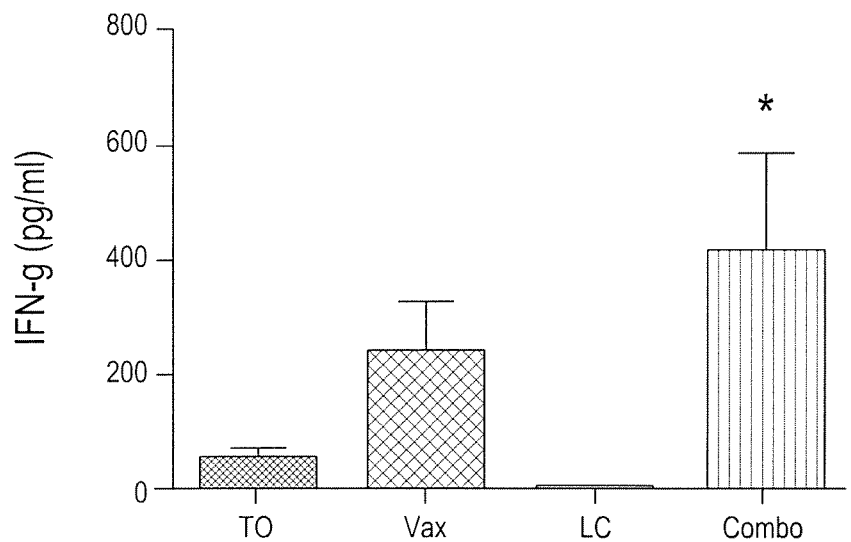
FIG. 16. Co-administration of LC enhances CD4 T cell responses to tumor vaccine.
Figure 16B:
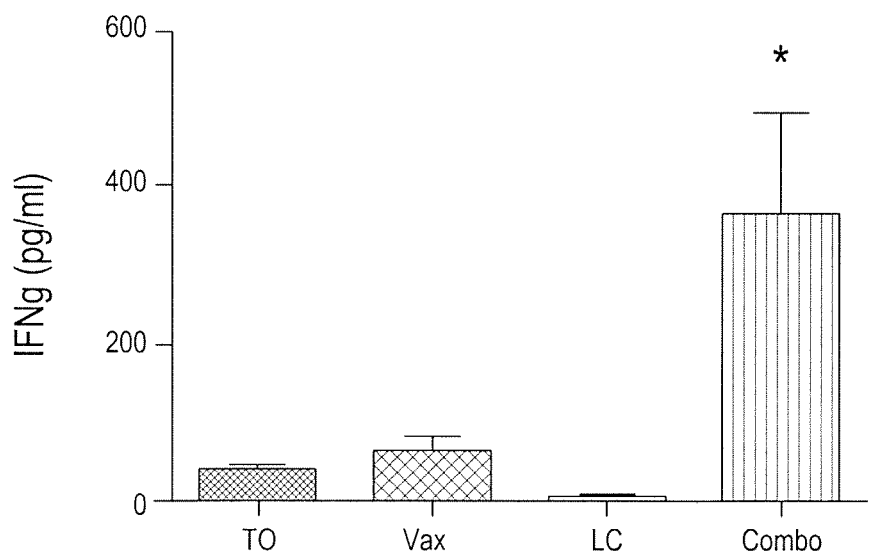

FIG. 16 demonstrates the enhanced CD4 T cell response to tumor cell lysates prepared from lysed lymphoma A20 cells. The combination of vaccine and MDSC inhibiting agent (LC) resulted in an IFN-g (pg/ml) level of about 425+/−124, while vaccine alone resulted in only a level of about 225 pg/ml+/−about 50. (FIG. 16A). FIG. 16B provides results achieved in animals when their spleen cells were restimulated with whole tumor cells, which tends to induce immune responses by CD8+ T cells. Similar enhancement of IFNg levels in MDSC depleting agent treated animal s receiving the vaccine were observed, compared to animals treated with vaccine alone.

Figure 17:
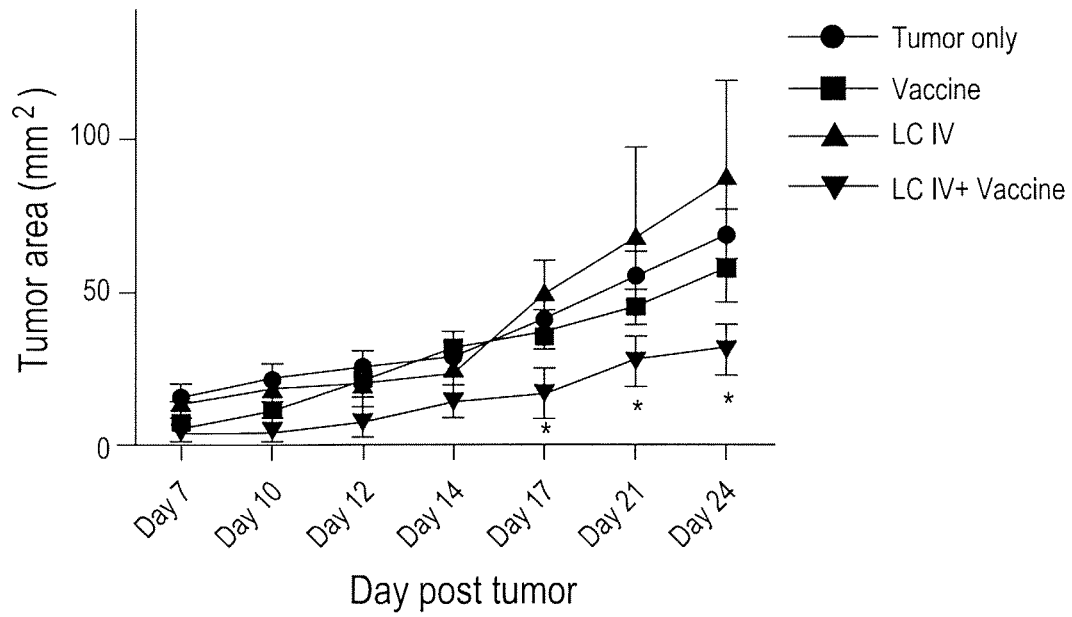
FIG. 17. LC co-administration significantly improves tumor vaccine efficacy: whole cell tumor vaccines.

Tumor size in animals treated with the whole tumor vaccines were also examined after treatment with vaccine or MDSC inhibiting agent (LC) plus vaccine treatment. The results of this study are presented in FIG. 17. The greatest suppression of tumor size and growth was again observed in animals treated with the MDSC inhibiting agent (LC) in combination with the whole cell tumor vaccines.

Figure 18:
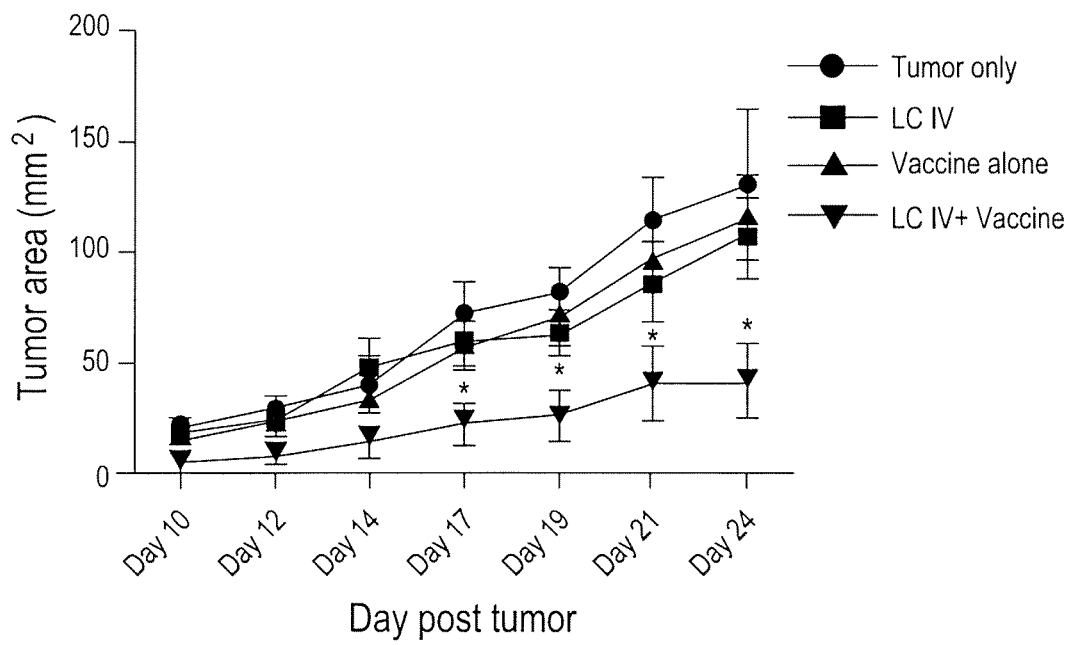
FIG. 18. LC co-administration significantly improves tumor vaccine efficacy: tumor cell membrane vaccine. A20 HA tumor growth; $10^6$ A20 HA on flank; 10 μg MPF/vaccine/week.

Tumor size in animals treated with a tumor cell membrane vaccine was also examined. These results are presented in FIG. 18. Similarly, the greatest suppression of tumor size and growth was again observed in animals treated with the MDSC inhibiting agent (LC) in combination with the tumor cell membrane vaccines.

Example 5

The MDSC Depleting Agents in Combination with Numerous Different Adjuvants Provides an Enhancement of Vaccine Adjuvancy The present example demonstrates the utility of the present invention for enhancing the immune response of an animal to a vaccine containing a diverse group of adjuvants, including by way of example, IFA (incomplete Freund's adjuvant), Alum, Alhydroge; MPL (Corrixa MPL adjvuant), DPIC (liposomal polyI:C adjuvant); and CLDC (cationic liposome-DNA complex adjvuant).

Figure 19:
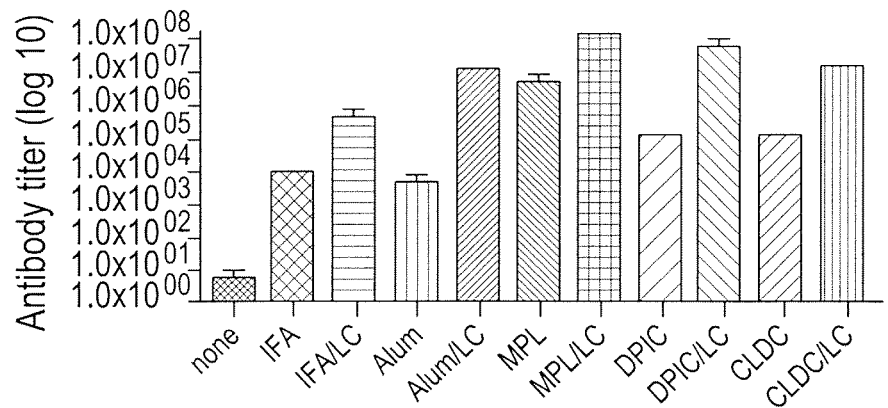
FIG. 19. Impact of MDSC depletion with liposomal clodronate on antibody responses to vaccination with various adjuvants. Key to adjuvants: IFA=incomplete Freund's adjuvant; Alum=Alhydrogel; MPL=Corrixa. MPL adjvuant; DPIC=liposomal polyI:C adjuvant; CLDC=cationic liposome-DNA complex adjvuant FIG. 20. Impact of MDSC depletion with liposomal clodronate on cytokine responses to following vaccination with various adjuvants.

Mice (n=4 per group) were vaccinated with 5 ug Ova protein admixed with adjuvant s.c. Half of the groups of animals were vaccinated and treated at the same time by i.v. administration of liposomal clodronate (LC), which is an effective myeloid derived suppressor cell (MDSC) depleting agent. (The optimal timing of LC administration relative to vaccine delivery was previously determined). The mice were then boosted with vaccine+/−LC 10 days later, then antibody responses to Ova were assessed by endpoint dilution ELISA 7 days after the boost. The data indicated that co-administration of LC with vaccination generated a strong increase in antibody titers for all 5 different adjuvants. The magnitude of the LC effect was greatest with the Alum adjuvant. These results are presented in FIG. 19. The ability of LC co-administration to enhance vaccine humoral responses with conventional adjuvants was relatively independent of adjuvant composition. It should also be noted that vaccination with Ova+LC elicited only modest humoral immune responses. Key to adjuvants: IFA=incomplete Freund's adjuvant; Alum=Alhydrogel; MPL=Corrixa MPL adjvuant; DPIC=liposomal polyI:C adjuvant; CLDC=cationic liposome-DNA complex adjvuant.

Figure 20:
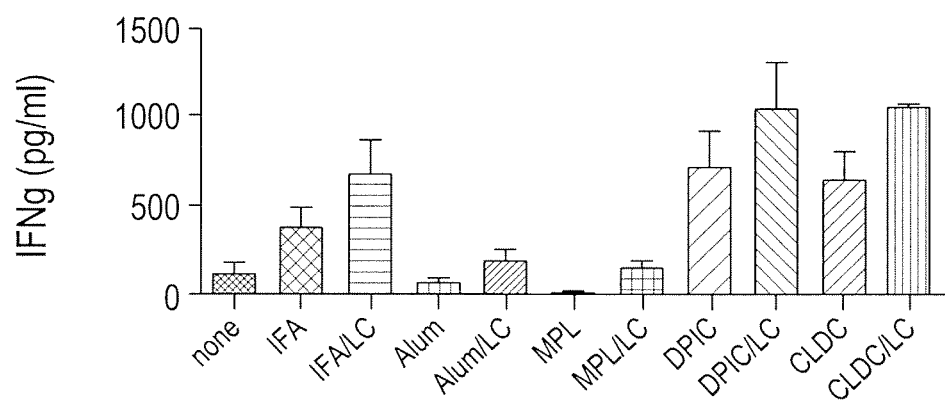

Mice (n=4 per group) were vaccinated with 5 ug Ova protein admixed with adjuvant s.c. Half of the groups of animals were vaccinated and treated at the same time by i.v. administration of liposomal clodronate (LC), which is an effective myeloid derived suppressor cell (MDSC) depleting agent. The optimal timing of LC administration relative to vaccine delivery was determined in previous studies. The mice were then boosted with vaccine+/−LC 10 days later, and the mice were euthanized 7 days later for assessment of T cell responses to Ova restimulation in vitro. Spleen cells were incubated with 50 ug/ml Ova in triplicate wells for 72 h, then supernatants were collected and IFN-γ concentrations determined by ELISA. The results are presented at FIG. 20. The data indicated that co-administration of LC with conventional vaccines generated stronger T cell recall IFN-γ responses than immunization with vaccine alone. This effect was observed for all 5 different adjuvants, and was particularly evident in the case of vaccines that elicited relatively small IFN-g responses on their own (eg, IFA, Alum, MPL). Thus, the ability of LC co-administration to enhance T cell responses is demonstrated to be independent of adjuvant composition.

Example 6

Vaccination Triggers Recruitment of MDSC Cells that can be Blocked with Adjuvant/Vaccine Additive (Myeloid Derived Suppressor Cell Inhibiting Agent)

The present example is provided to demonstrate the utility of the present invention for blocking the vaccine inhibitory action of infiltrating myeloid derived suppressor cells (MDSC) (also known as vaccine elicited myeloid cells, or MDSC), with a detectable augmentation of vaccine immunity in vivo. In particular, the present example presents data demonstrating that the interference with the MDSC recruitment will augment vaccine immunity by interfering with the recruitment of MDSC to the lymph nodes after vaccination. In addition, the data presented here presents direct in vivo data demonstrating that the presence of the MDSC in the vaccine draining lymph nodes interferes with T cell responses. T cell activation in the lymph nodes is essential to developing a good vaccine response. The present example also provides evidence of the utility of the present invention for augmenting the effectiveness of a cancer vaccine by including the vaccine/adjuvant additives (the MDSC inhibitory agents) in vaccination.

Figure 21:
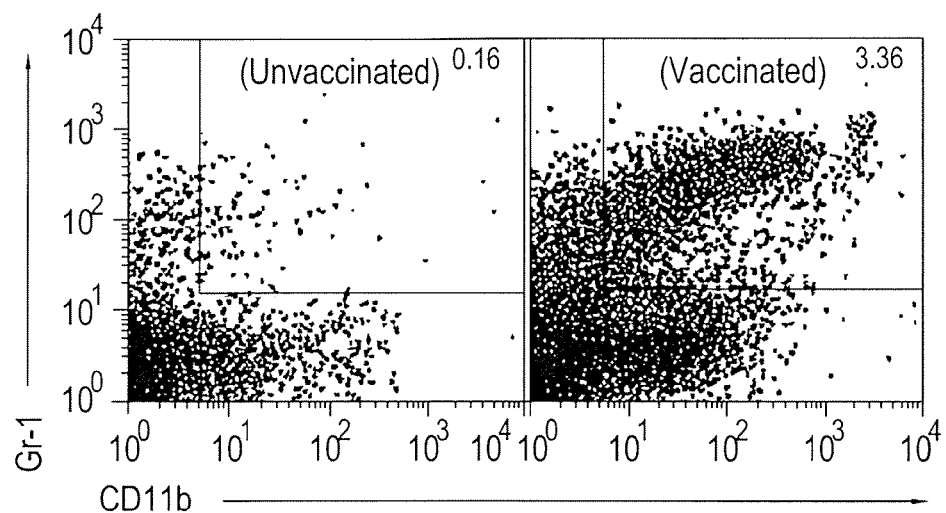
FIG. 21. Vaccination triggers recruitment of myeloid cells (monocytes and neutrophils) into draining lymph nodes.

Mice were vaccinated in the footpad and 24 h later, the vaccine draining LN was collected and cellular responses assessed using flow cytometry. A strong infiltrate of Cd11b+/Gr-1+ myeloid cells (MDSC) in the lymph nodes (LNs) of vaccinated mice was observed. FIG. 21 demonstrates the increase in myeloid cell infiltration in vaccinated animals (Right panel) compared to non-vaccinated animals (Left panel).

Figure 22:
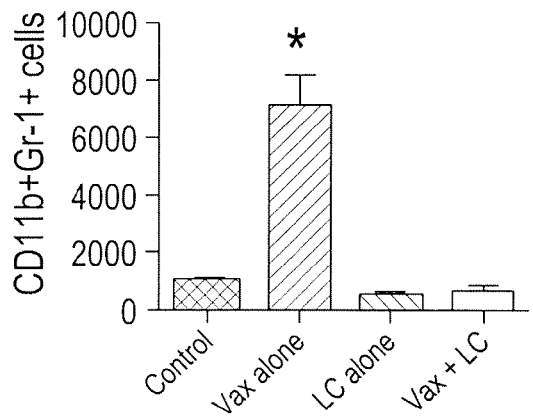
FIG. 22. Administration of liposomal clodronate (LC) efficiently depletes inflammatory myeloid cells from the vaccine draining lymph nodes.

Next, a study was done to demonstrate that treatment with the adjuvant/vaccine additive (MDSC inhibiting agent) blocked the infiltration of cells to lymph nodes (LN). Mice (n=4 per group) were vaccinated and at the same time treated with LC alone, or LC+vaccine. In the draining LNs of mice that received the vaccine only, there was a large increase in MDSC. However, in the LNs of vaccinated mice also treated with LC, the increase in MDSC was also completely blocked (FIG. 22).

Example 7

LC Administration Generates Significant Increase in Antibody Response and T Cell Response to Vaccination Augmented with an MDSC Inhibiting Agent The present example is provided to demonstrate the utility of the inventor for enhancing antibody response and T cell response to a vaccine in an animal.

Figure 23:
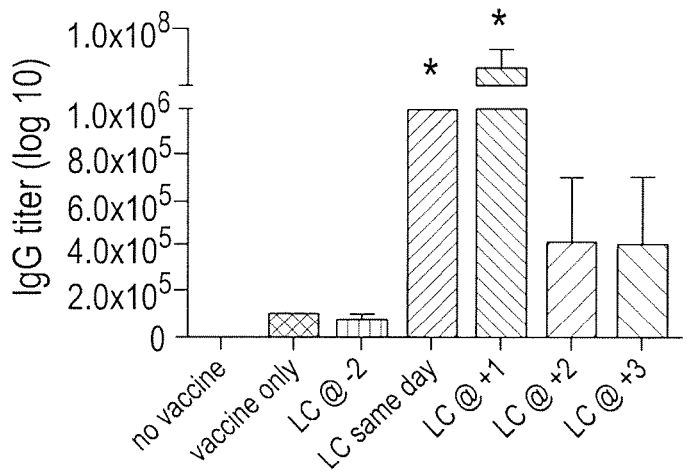
FIG. 23. LC administration generates significant increases in antibody responses to vaccination when administered at the time of vaccination of within 1-2 days after vaccination.
Figure 24:
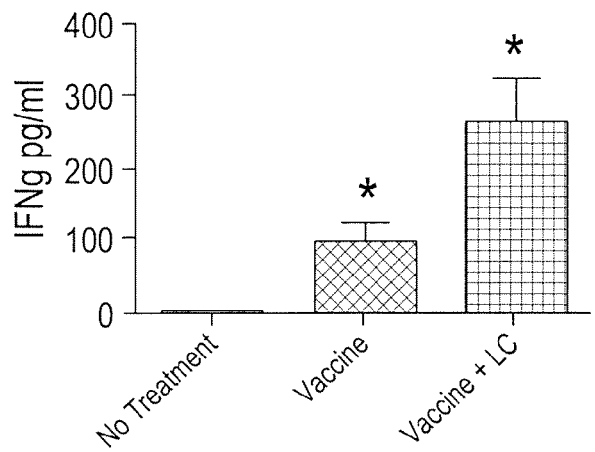
FIG. 24. Administration of LC at the time of vaccination significantly increases T cell responses to vaccination.

Antibody Response:

Mice were vaccinated and treated with LC at various time points before or after vaccination. Only LC treatment at the time of vaccination or shortly thereafter was effective in improving vaccine responses (antibody titers), consistent with the idea that depletion of the MDSC population is critical for enhancing vaccine efficacy (FIG. 23).

T Cell Response: Draining LN cells were collected from control and vaccinated mice, as well as from vaccinated mice also treated with LC at the time of vaccination. The LN cells were incubated in vitro with the vaccine antigen (Ova) and IFN-g production by the T cells was assessed 3 days later. Vaccinated mice treated with LC generated significantly higher amount of IFN than T cells from vaccinated only mice, indicative of increased T cell responses to the vaccine antigen.

Example 8

T Cell Proliferation is Inhibited after Vaccination in Vivo, and not Inhibited after Vaccination Together with an MDSC Inhibiting Agent The present example demonstrates that T cell proliferation after vaccination may be improved in the presence of the MDSC inhibitory agents after injection, and thus, enhance immune response to the vaccine.

Figure 25:
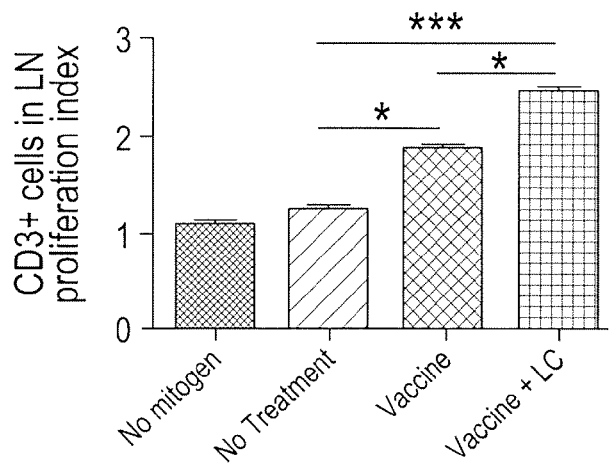
FIG. 25. Vaccination induces the recruitment of inflammatory myeloid cells into the draining LN, which results in suppression of T cell proliferative responses compared to mice that were vaccinated and treated concurrently with LC to deplete inflammatory myeloid cells.

Mice were vaccinated, then 24 h later Lymph nodes (LN) were collected and the LN cells were labeled with the dye CFSE. Flow cytometry was then used to determine how many CD3+ T cells underwent cell division during a 72 h in vitro incubation period. In LNs depleted of MDSC by LC treatment, T cell proliferation was significantly higher than in the LNs from vaccinated only (no LC) mice. This data is shown in FIG. 25.

Example 9

Production of Chemokines MCP-1 (CLL2)

The present example demonstrates that the presence of the MDSC inhibiting agents also induces the production of chemokines, compounds that regulate monocyte recruitment.

Figure 26:
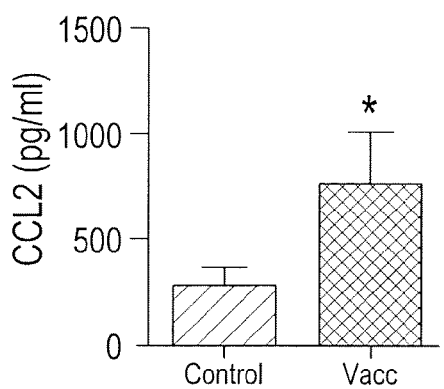
FIG. 26. Vaccination induces production of the chemokine MCP-1 (CLL2).

FIG. 26 presents the data from this study. Vaccine draining LNs were harvested 3 h after vaccination and release of CCL2 (the primary chemokine regulating monocyte recruitment) was measured. Chemokine (C-C motif), 2 (CCL2) is a small cytokine belonging to the CC chemokine family that is known as monocyte chemotactic protein-1 (MCP-1) and small inducible cytokine AZ. CCL2 recruits monocytes, memory T cells, and dendritic cells to sites of tissue injury, infection and inflammation.

Vaccination triggered a significant increase in CCL2 release from the draining LN, which could serve as an important signal for MDSC recruitment. Therefore, it is anticipated that blocking CCL2 release with a CCL2 inhibitory agent will inhibit recruitment of myeloid derived suppressor cells (MDSC). As a result, it is expected that CCL2 inhibitory and/or blocking agents with therefore also be useful as an additive and/or adjuvant in enhancing immune response in an animal to a vaccine.

Example 10

The MDS Cell Inhibiting Agents Impair Mobilization of Myeloid Derived Suppressor Cells The present example establishes that the invention may be used to immobilize populations of myeloid derived suppressor cells in vivo.

Figure 27:
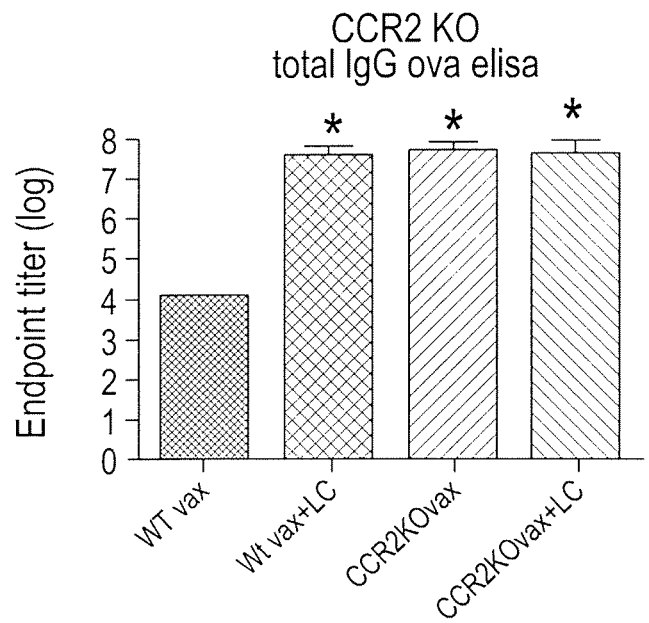
FIG. 27. Vaccine responses are increased in CCR2−/− mice that are impaired in their ability to mobilize monocytes in response to inflammation.

Studies were done to compare the ability of mice unable to mobilize MDS cells (MDSC) due to a lack of expression of the CCL2 receptor (ie, CCR2−/− mice). These mice do not generate monocyte infiltration in response to inflammatory stimuli. The ability of CCR2-mice to make antibody responses to vaccination was compared to that of wild type (WT) mice, and the CCR2− mice were found to be significantly better (FIG. 27). This inability of these CCR2− animals to mobilize monocytes is demonstrated in this data to contribute to enhanced immunity to vaccination.

In addition, the CCR2−/− mice did not respond to LC treatment. This establishes that inhibition of monocyte migration has the same effects on vaccination as actually eliminating monocytes with an MDSC inhibitory agent. These results are important because they indicate that interfering with monocyte migration, as for example by administering an MDSC inhibitory agent, e.g., small molecule such as a CCR2 inhibitor (such as, for example, RS1028595, PF-04178903, or those listed in Higgins et al., (2007, Table 1) drug, can improve vaccine responses as effectively as eliminating monocytes outright with liposomal clodronate (LC) or other bisphosphonate drug.

By way of example, such small molecule drugs may include RS1028595, Sigma Aldrich.

Example 11

MDSC Inhibiting Agents with Cancer Vaccines

The present example demonstrates that the MDSC inhibiting agents used in combination with cancer vaccines will improve the anti-cancer activity of the cancer vaccine.

Figure 28:
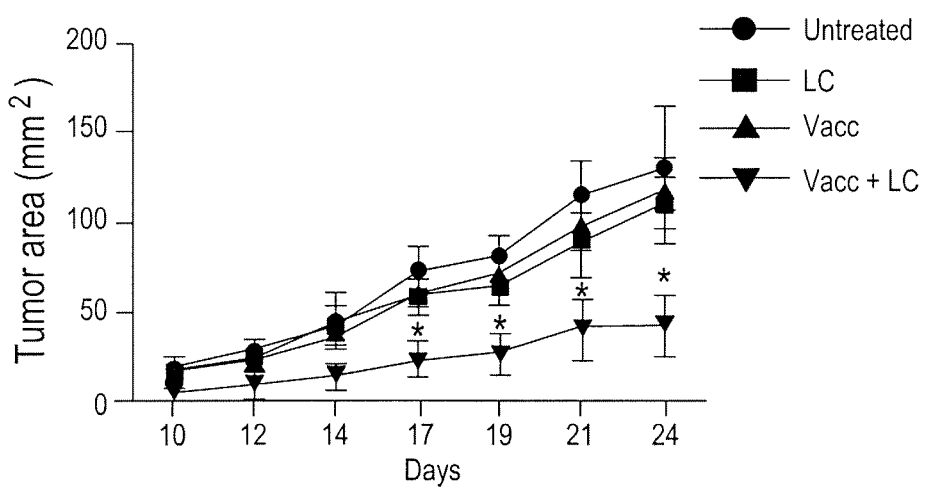
FIG. 28. Elimination of inflammatory myeloid cells using LC significantly improves the activity of cancer vaccines FIG. 29. Combined vaccination and inflammatory myeloid cells depletion increases IFN-γ responses by CD4 T cells from vaccinated mice. A20 HA vaccine study. IFN-γ release in response to SFERFEIFPKE peptide (Class II restricted HA peptide)

Studies were conducted to determine whether co-administration of LC with a tumor vaccine could improve responses to vaccination with an autologous tumor vaccine prepared with A20 cell membrane proteins. Mice with established A20 lymphoma tumors were vaccinated once weekly, with or without LC treatment, and tumor growth rates were monitored. The combined treatment with tumor vaccine and LC significantly slowed tumor growth, compared to treatment with either vaccine or LC alone (FIG. 28).

Example 12

Figure 29:
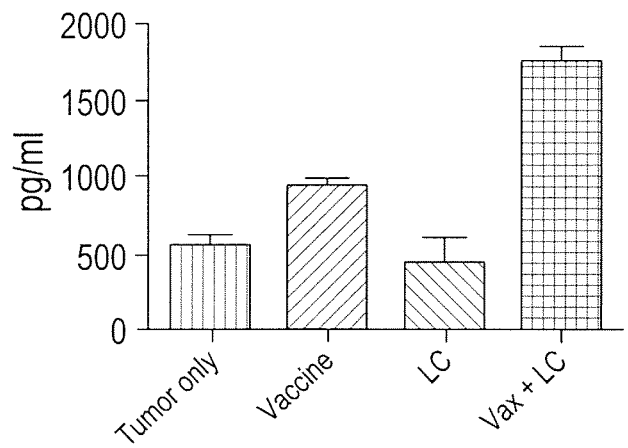

IFN-Gamma Response in MDSC Depleted Animals Vaccinated with HA Peptide Vaccine The effects of MDSC depletion and vaccination on the ability of spleen CD8 T cells to mount a recall response against tumor antigens is demonstrated. FIG. 29 presents the results of the effects of MDSC depletion and vaccination on the ability of spleen CD4 T cells to mount a recall response against soluble tumor antigens. The A20-HA tumor used in these studies was transfected with the influenze HA gene, which permitted the use of this antigen as a surrogate tumor antigen. The ability of vaccinated mice to mount an IFN-γ recall response against the MHC class II restricted HA peptide (SFERFEIFPKE) was assessed.

A significant increase in INF-γ production in the vaccinated mice was observed, and also a significant further enhancement in this response in the vaccine+LC treatment group. These data demonstrate that vaccination plus MDSC depletion with LC significantly augments CD4 T cell responses to a tumor antigen (FIG. 29).

Figure 30:
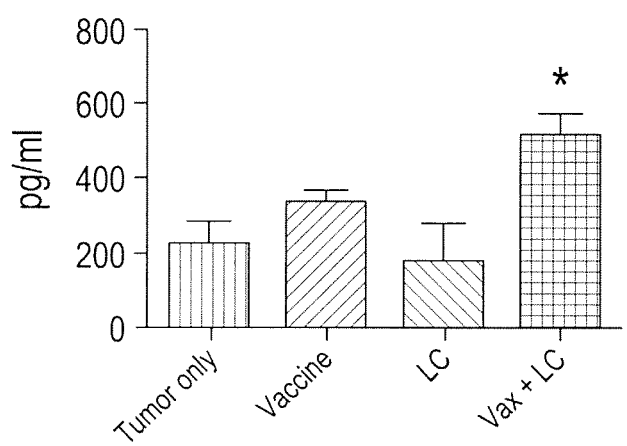
FIG. 30. Combined vaccination and inflammatory myeloid cells depletion increases IFN-γ responses by CD8 T cells from vaccinated mice.

In another study, the effects of MDSC depletion and vaccination on inability to spleen CD8 T cells to mount a recall response agent tumor analysis was assessed. The A20-HA tumor used in these studies was transfected with the influenza HA gene, which permitted the use of this antigen as a surrogate tumor antigen. The ability of vaccinated mice to mount an IFN-γ recall response against the MHC class I restricted HA peptide (IYSTVASSL) was also examined. A modest increase in IFN-γ production in vaccine only mice following restimulation with the MHC I peptide was observed (See FIG. 29, 950+/−40 pg/ml IFNg release). However, there was a significant enhancement in response in the vaccine+LC treatment group (1,750 pg/ml IFNg release+/−50 pg/ml) (FIG. 30).

These data indicate that vaccination plus MDSC depletion with LC significantly augments CD8 T cell responses to a tumor antigen. (FIG. 30).

Example 13

MDSC Depletion Augments Generation of Tumor Specific Antibodies Following Tumor Vaccination The present example is provided to demonstrate the use of the present MDSC depleting agents in augmenting production of anti-tumor antibodies.

Figure 31:
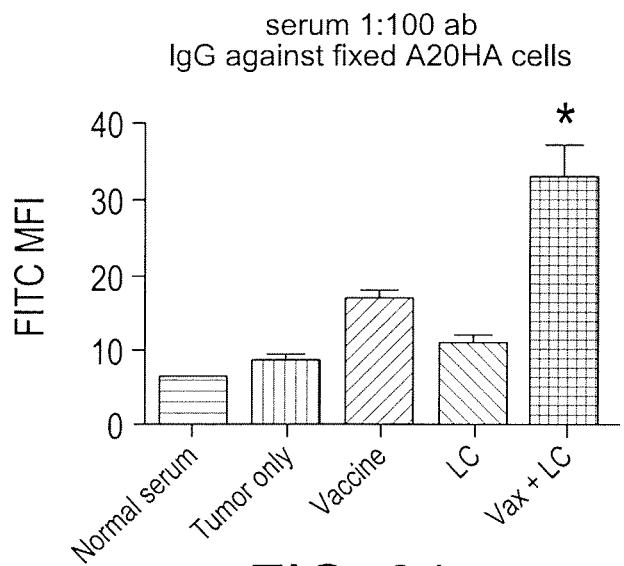
FIG. 31. Inflammatory myeloid cells depletion augments generation of tumor-specific antibodies following tumor vaccination. Serum 1:100 ab IgG against fixed A20HA cells cells.

The impact of MDSC depletion using LC on the magnitude of anti-tumor antibody responses is demonstrated. Serum from vaccinated and control mice was evaluated for tumor surface binding to fixed A20 tumor cells using flow cytometry. Vaccination+LC administration significantly increased the generation of antibodies directed to cell surface epitopes on the A20 tumor cells, compared to vaccination alone. (FIG. 31).

Figure 32:
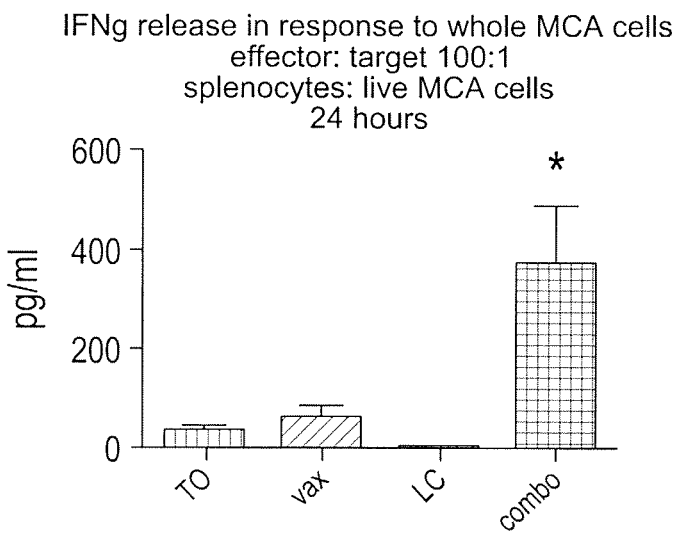
FIG. 32. Combined vaccination and LC administration also significantly increases T cell responses to vaccination against MCA sarcoma in mice. IFN-γ released in response to whole MCA cells effected:target 100:1 spenocytes:live MCA cells 24 hours.

Experiments were also done to determine whether MDSC depletion using LC could augment tumor vaccine responses in a different strain of mice (MDSC) and against a different tumor type (MCA-205). Mice were vaccinated with an autologous MCA vaccine and treated with or without LC. After 2 immunizations, spleens were collected and restimulated in vitro with MCA tumor cells and IFN-γ, indicative of enhanced T cell immunity following MDSC depletion. These results also indicate that the effectiveness of MDSC depletion with LC is not limited to a certain strain of mouse or a certain tumor type (FIG. 32).

This HA molecule is not a tumor antigen. It is from influenza. It is actually used as a surrogate for a tumor antigen in the A20 model used herein. The peptides are HA peptides that are used here to distinguish CD4 from CD8 T cell responses.

Example 14

Myeloid Suppressor Cell Inhibitory Agents for Use with Vaccine Regimens

Any variety of small molecules that are capable of inhibiting the action of myeloid suppressor cell migration, accumulation and viability is anticipated to be useful as the adjuvant additive of the present invention. By way of example, the following MDSC agents may include drugs that block monocyte release from bone marrow (CCL2 or CCR2 inhibitors or competitors, M-CSF inhibitors, GM-CSF inhibitors). Further examples include compounds that block chemokines that mobilize neutrophils from the bone marrow, including inhibitors of IL-8, KC, and G-CSF.

Vaccine Regimens: It is anticipated that the MDSC agents described herein may be used to boost immune response to virtually any vaccine regimen in an animal. By way of example, these vaccine include vaccines for: 1.) any infectious agent (bacterial, viral, fungal, protozoal); 2.) vaccines for allergy, 3.) vaccines for autoimmune disorders; 4.) vaccines for toxins; 5.) vaccines for addictive substances (eg., nicotine, alcohol, caffeine, etc.).

While not intended to be exhaustive, the following presents exemplary vaccines for this purpose.

Exemplary Infectious Pathogens

The present example demonstrates the utility of the present invention with disease associated with a wide variety of infectious pathogens and biological toxins, including by way of example and not exclusion, tetanus, influenza, rabies, viral hepatitis, diphtheria, anthrax, *Streptococcus pneumoniae* infection, malaria, leishmaniasis, ricin toxicosis, and Staphylococcal enterotoxin B toxicosis.

TABLE 2 Classification of Common Vaccines for Humans Disease or Pathogen Type of Vaccine Whole Organisms:

Bacterial cells: Cholera Inactivated Plague Inactivated Tuberculosis Attenuated BCG+ *Salmonella typhi* Attenuated Viral Particles: Influenza Inactivated Measles Attenuated Mumps Attenuated Rubella Attenuated Polio (Sabin/OPV) Attenuated Polio (Salk/IPV) Inactivated V. zoster Attenuated Yellow fever Attenuated Type of Vaccine (Purified) Macromolecules Toxoids: Diphtheria Inactivated exotoxin Tetanus Inactivated exotoxin acellular Pertussis Inactivated exotoxins Capsular polysaccharide: *Haemophilus influenzae* b polysaccharide+protein carrier *Neisseria meningidis* Polysaccharide *Streptococcus pneumoniae* 23 distinct capsular polysaccharides Surface antigen: Hepatitis B Recombinant surface antigen (HbsAg)+*Bacillus* Calmette-Guerin (BCG) is an antiviral strain of *Mycobacterium bovis*.

Vaccines for Disease Associated with Viral Infections

Influenza—Influenza is an acute febrile respiratory disease resulting from infection with the influenza virus. Current influenza vaccines use aluminum adjuvants. To enhance the efficacy of vaccines, several adjuvants have been examined. For example, the oil-in-water emulsion MF59 has been reported to improve vaccine immunity (Higgins (1996); Martin (1997), though it does not completely solve the low efficiency of the influenza vaccine in the elderly (Banzhoff (2003). A synthetic peptide, GK1, derived from *Taenia crassiceps cysticerci* was reported to enhance the immune response accompanying influenza vaccination in both young and aged mice (Segura-Velasquez (2006).

As part of the present invention, an influenza vaccine may be provided that comprises the MDS inhibiting agent combined with an immunologically effective amount of an influenza antigen with an adjuvant. By way of example, such an influenza antigen may comprise a current influenza virus combination of antigens of an H5N1 (hemagglutinin [HA] subtype 1; neuraminidase [NA] subtype 1), and H3N2 influenza A virus, and an influenza B virus. This preparation and other influenza antigen preparations are described in Palese (2006). This article and all of its teachings are incorporated herein by reference.

Rabies—Rabies is a devastating neurological disease that is caused by infection with the rabies virus. Vaccination against rabies typically utilizes inactivated virus and an aluminum adjuvant. A lipoid adjuvant of the oil-in-water type, based on squalene, significantly increased the immunologic response of mice to vaccination with an inactivated virus vaccine when compared to vaccination using an aluminum salt adjuvant (Suli, 2004). An adjuvant based on glycopeptidolipids extracted from *Mycobacterium cheloniae* enhanced the immune response of mice to vaccination with an inactivated rabies virus vaccine (de Souza Matos (2000).

As part of the present invention, a rabies vaccine may be provided that comprises the MDSC inhibiting agent combined with an immunologically effective amount of a rabies antigen. By way of example, a rabies antigen may comprise an inactivated rabies virus. One example of an inactivated rabies virus vaccine antigen that may be used in the present formulations is described in de Souza Matos (2000).

3. Viral Hepatitis—Viral hepatitis, particularly that caused by Hepatitis B virus, is a serious health problem with over 300 million people affected worldwide. Vaccination offers hope for effective prophylaxis. Peptide epitopes of the virus stimulated a significant immune response when fused with heat shock protein 70 from *Mycobacterium tuberculosis* as an adjuvant (Peng (2006). Unmethylated CpG dinucleotides were effective as an adjuvant with hepatitis B antigen in aged mice (Qin (2004); and a vaccine consisting of hepatitis B virus antigens and an immunostimulatory DNA sequence is in human clinical trials (Sung (2006). In development of an intranasal vaccine, it was shown that DL-lactide/glycolide copolymer microspheres with chitosan were an effective adjuvant for a vaccine based on recombinant Hepatitis B surface protein (Jaganathan (2006).

As part of the present invention, a viral hepatitis vaccine may be provided that comprises the MDSC inhibiting agent combined with an immunologically effective amount of a viral hepatitis antigen. By way of example, such a hepatitis antigen may comprise recombinant hepatitis B surface protein. By way of example, such a hepatitis B surface protein antigen is described in Jaganathan, (2006), which reference is specifically incorporated herein by reference.

Vaccines for Disease Associated with Bacterial Infections:

Diphtheria—A respiratory disease characterized by dysnepea, weakness, and pyrexia, diphtheria is the result of infection with *Corynebacterium diphtheriae*, bacteria which produces a toxin that is carried hematogenously through the body. Immunization against diphtheria is frequently combined with immunization against tetanus and pertussis; these vaccines typically contain aluminum salt adjuvants (Sugai (2005). Unmethylated CpG dinucleotides were effective as an adjuvant in a diphtheria-tetanus-pertussis vaccine and shifted the immune response toward cell-mediated immunity in mice immunized intraperitoneally (Sugai (2005). Trials to reduce adverse side-effects related to the aluminum salt adjuvant of a vaccine consisting of diphtheria toxoid, tetanus toxoid, and purified *Bordetella pertussis* antigens including pertussis toxoid showed that reduction of the aluminum salt content of the vaccine resulted in reduced geometric mean antibody concentrations to the relevant antigens, but did not result in reduction of local or general side effects (Theeten (2005). Monophosphoryl lipid A was shown in mice to effectively serve as an adjuvant for diphtheria toxin in mice (Caglar (2005).

As part of the present invention, a diphtheria vaccine may be provided that comprises the MDSC inhibiting agent combined with an immunologically effective amount of a diphtheria antigen. By way of example, a diphtheria antigen may comprise a diphtheria toxoid. One example of a diphtheria toxoid that may be used in the practice of the present invention is described in Theeten (2005).

2. Anthrax—Anthrax is a disease caused by the bacterium, *Bacillus anthracis*. Specifically, the bacterium produces a toxin which results in hemorrhagic necrosis of lymph nodes, hematogenous spread, shock, and death. A vaccine consisting of one subunit (protective antigen) of this toxin was shown to protect mice when combined with a microparticle adjuvant administered by either the intramuscular or intranasal routes (Flick-Smith (2002). Further, vaccination protected mice against infection with *B. anthracis* spores. While the aluminum salt-adjuvanted anthrax-vaccine-adsorbed is the only anthrax vaccine licensed in the United States, major drawbacks exist, including a very lengthy and complicated dosing schedule, followed by annual booster injections. Further, the aluminum adjuvant of anthrax vaccine has been linked to Gulf War Illness among veterans of the 1991 conflict (Petrik (2007)).

As part of the present invention, an anthrax vaccine may be provided that comprises the MDSC inhibiting agent combined with an immunologically effective amount of an anthrax antigen and an adjuvant. By way of example, such an anthrax antigen may comprise the one subunit (protective antigen) of the *Bacillus* anthracia bacterium. One such particular antigenic subunit is described in Flick-Smith (2002).

3. *Streptococcus pneumoniae*—A bacterial pathogen of particular importance to the elderly and young adults, *Streptococcus pneumoniae* causes disease including sepsis and pneumonia, otitis media and meningitis. Vaccines typically involve adsorption of *S. pneumoniae* antigens to aluminum salt adjuvants, and reduced aluminum salt content led to reduced immunogenicity of *S. pneumoniae* vaccines (Levesque (2006). In human trials, IL-12 failed to improve the immune response to a pneumococcal polysaccharide vaccine; and IL-12 was associated with a high incidence of local and systemic side effects in humans (Hedlund (2002). Intranasal immunization against *S. pneumoniae* has been shown to be an effective method for preventing infection and disease, with unmethylated CpG dinucleotides serving as an effective adjuvant for an intranasal polysaccharide-protein conjugate vaccine (Sen (2006). Likewise, IL-12 and the B-subunit of cholera toxin were both shown to enhance efficacy of intranasally-administered preparations of *S. pneumoniae* antigens (Sabirov (2006); Pimenta (2006)).

As part of the present invention, a pneumonia vaccine may be provided that comprises the MDSC inhibiting agent described herein together with a vaccine adjuvant combined with an immunologically effective amount of a pneumococcal antigen. By way of example, such a pneumococcal antigen may comprise a pneumococcal polysaccharide antigen. One form of a pneumococcal polysaccharide antigen is described in Hedlund (2002). This pneumococcal antigen may used as part in combination with the herein described MDSC inhibiting agent with an adjuvant containing vaccine preparation.

Vaccines for Diseases Associated with Parasitic Infections

Malaria—Malaria affects millions of people worldwide and each year, 1-2 million people die from the disease caused by *Plasmodium falciparum*. Thus, the need for prophylactic measures has led to great interest in anti-malaria vaccines. The apical membrane antigen, a malaria vaccine candidate, was reported to have an enhanced immunogenicity by the aluminum salt adjuvant Alhydrogel (HCl Biosector, Denmark); and this adjuvant effect was further enhanced, and shifted from a Th1 response to a mixed Th1/Th2 response, by inclusion of the adjuvant CpG oligodeoxynucleotide (Mullen (2006). Alhydrogel and Montanide ISA 720 (Seppic, France) were compared in rhesus monkeys as adjuvants for a vaccine based on protective epitopes from the circumsporozoite protein of *P. falciparum*. Though Montanide ISA 720 induced superior immune responses, the formation of sterile abscesses at injection sites were noted as a significant disadvantage (Langermans (2005). Other studies with a circumsporozoite protein vaccine conducted in rhesus monkeys showed that some novel oil-in-water adjuvants with components of immunostimulants 3-deacetylated monophosphoryl lipid A (3D-MPL) and the saponin *Quillaja saponaria* 21 (QS21) were safe and stimulated improved antibody responses (Stewart (2006). Some of these same oil-in-water adjuvants improved the immune response to a vaccine constructed of the *P. falciparum* antigen, Liver Stage Antigen-1 (Brando (2006).

As part of the present invention, a malarial vaccine may be provided that comprises the MDSC inhibiting agent together with a vaccine adjuvant combined with an immunologically effective amount of a malarial antigen. By way of example, such a malarial antigen may comprise a *P. falciparum* antigen Liver Stage Antigen-1. This antigen is described in detail in Brando (2006), this article being specifically incorporated herein by reference. This antigen may be combined with the myeloid derived suppressor cell inhibiting agent material described herein as an adjuvant to provide an anti-malarial vaccine as described herein.

2. Leishmaniasis—Leishmaniasis is a parasitic disease associated with infection by a species of parasites from the *Leishmania* genus. A large spectrum of clinical disease forms can result from infection, ranging from cutaneous lesions to fatal visceral forms. In the absence of effective, non-toxic treatments, great effort has been given to vaccine development. Vaccines based on DNA of the parasite have been shown to induce partial protection; aluminum phosphate adjuvant has no effect on the humoral response to this vaccine, but has been reported to slightly increase the cellular immune response and protection against infection in a mouse model (Rosado-Vallado (2005). In evaluations in rhesus monkeys using a soluble *Leishmania* antigen and alum with IL-12 as adjuvants, it was shown that the adjuvants improved protective immunity, though transient nodules developed at the site of subcutaneous injection (Kenney (1999). CpG oligodeoxynucleotides served as an effective adjuvant for a vaccine consisting of live, nonattenuated *L. major* organisms alone or in combination with lysates of heat-killed *L. major* promastigotes, either without or bound to alum (Mendez (2003). Partial protective immunity was stimulated, but mice receiving alum-containing vaccines developed large dermal lesions that required up to 10 weeks to heal.

As part of the present invention, an anti-parasitic infection associated disease vaccine may be provided that comprises the MDSC inhibiting agent together with a vaccine adjuvant combined with an immunologically effective amount of a Leishmaniasis antigen, or any of the other antigenic species described above. By way of example, a Leishmaniasis antigen may comprise the Leishmaniasis antigen described in detail in Kenny (1999), which article is specifically incorporated herein by reference.

Vaccines for Disease Associated with Biological Toxins

1. Ricin—Ricin is a toxin produced naturally by the seeds of the castor bean plant, *Ricinus communis*. When humans or animals are exposed to the toxin, severe respiratory distress and death may result. Because of its potency and ability to be administered via aerosol, ingestion, or injection, ricin is considered a powerful bioweapon. Though there is presently no approved commercial vaccine for ricin, pilot trials in humans have examined the use of recombinant, non-toxic forms of one of the subunits of ricin (Vitetta (2006). This preparation was administered without an adjuvant and elicited ricin-neutralizing antibodies in some of those tested, particularly at higher doses. However, all dose groups were found to result in significant side-effects, including myalgia and headache. Ricin toxoid adjuvantized by liposomal encapsulation was found to induce a stronger immune response when administered intra-tracheally than the vaccine adjuvantized with an aluminum salt adjuvant (Griffiths, 1997).[29] A vaccine consisting of a deglycosylated chain A ricin (DCAR) and the adjuvant LTR72, a mutant of the heat-labile enterotoxin of *Escherichia coli*, resulted in a stronger antibody response of vaccinated mice to ricin, but did not result in improved protection against lung injury when challenged with ricin (Kende (2006).

As part of the present invention, an anti-ricin vaccine may be provided that comprises the MDSC inhibiting agent together with a vaccine adjuvant as described herein combined with an immunologically effective amount of a ricin toxoid antigen. By way of example, such a ricin toxoid antigen is described in detail in Griffiths (1997), which article is specifically incorporated herein by reference.

2. Staphylococcal enterotoxin B (SEB)—SEB is produced by the bacteria, *Staphylococcus aureus* and is associated with food poisoning. Incorporation of SEB toxoid into biodegradable poly(DL-lactide-co-glycolide) microspheres enhanced the immune response of mice to a degree similar to SEB toxoid adsorbed to alum and combined with complete Freund adjuvant (Eldridge, 1991). Similarly, SEB toxoid was effectively adjuvantized by incorporation into polylactic polyglycolic acid copolymer nanospheres; the resulting immune response was comparable to that achieved by using alum as an adjuvant (Desai (2000).

As part of the present invention, an anti-toxin-associated disease vaccine may be provided that comprises the MDSC inhibiting agent together with a vaccine adjuvant combined with an immunologically effective amount of an antigen such as ricin toxoid or SEB toxoid as antigen. By way of example, such antigens are described in detail in Vitetta (2006) and Eldridge (1991), the teachings of which are specifically incorporated herein by reference.

Vaccines for Diseases Associated with Prions:

In some embodiments, the invention provides an adjuvant preparation that is suitable for use in combination with a prion-associated disease. By way of example, such prion associated diseases include, all of which are classified as transmissible spongiform encephalopathies, bovine spongiform encephalopathy, scrapie, cervid chronic wasting disease and Creutzfeld-Jakob disease.

Although prions use immune and lymphoreticular cells to gain access to the brain (Aguzzi, 2003), existing evidence suggests that humoral immune responses can suppress infection. In particular, antibodies to the cellular prion protein (PrPc) are known to inhibit prion propagation (Petetz, 2001; Enari, 2001). Still, host tolerance to endogenous PrPc remains a major obstacle to active vaccination. In mice, vaccination with recombinant PrPc antigens such as peptides and polypeptides stimulated only weak immune responses. Co-administration of prion antigens with adjuvants such as Freund's (Polymenidou, 2004; Koller, 2002; Sigurddson, 2002; Gilch, 2003; Hanan, 2001; Hanan, 2001; Souan, 2001; Arbel, 2003); Montanide IMS-1313 (Schwartz, 2003); TiterMax®, a combination of a proprietary block copolymer CRL-8941, squalene, a metabolizable oil, and a unique microparticulate stabilizer (Gilch, 2003); and CpG oligonucleotides (Rosset, 2004) all failed to induce strong immune responses.

It is anticipated that the presently described MDSC inhibitory agents may included with an adjuvant preparation together with the prion protein (PrPc) to provide an improved vaccine against prion-associated infections.

Example 15

CCR2 Inhibitors and/or CCR2 Antagonists as Vaccine/Adjuvant Additives

The present example demonstrates the utility of the invention for providing the use of CCR2 inhibitors and/or CCR2 antagonists as an adjuvant or as an additive to a vaccine treatment regimen. The present disclosure outlines the use of the small molecule myeloid derived suppressor inhibiting agent, CCR2 inhibitor RS1028595 (Sigma Aldrich), as a vaccine/adjuvant additive or adjuvant. It is expected that virtually any CCR2 inhibitor and/or antagonist that demonstrates the myeloid derived suppressor cell inhibiting activity described herein, and especially an activity for blocking the migration of myeloid derived suppressor cells to draining lymph nodes, or interferes with inflammatory monocytes trafficking, would be useful and within the reasonable scope of the present preparations and methods.

Applicants incorporate specifically herein by reference the disclosure of Higgins et al. (2007) (Chemokine Biology—Basic Research an Clinical Application, Vol. II, Birkhauser Verlag Basel Switzerland, "Small molecule CCR2 antagonists", pg. 115-123). While not intending to be limited in any way by this exemplary set of CCR2 molecules, Table 1 below presents a number of CCR2 antagonists that are considered to be within the scope of the present adjuvant/vaccine additives and adjuvants described as part of the present vaccine treatment regimens.

TABLE 1

| Company | CCR2 Antagonists |
| --- | --- |
| Roche/Iconix | 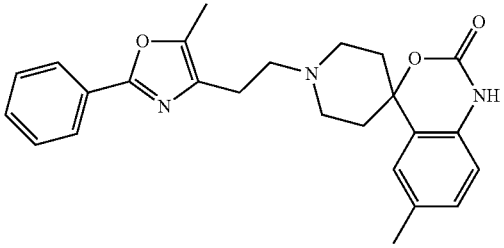 [SMILES: Cc1ccc2c(c1)C1(CCN(CCc3nc(-c4ccccc4)oc3C)CC1)OC(=O)N2]<br>CCR2 IC(50) - 89 nM bind, 210 nM taxis |
| Millennium/Pfizer | 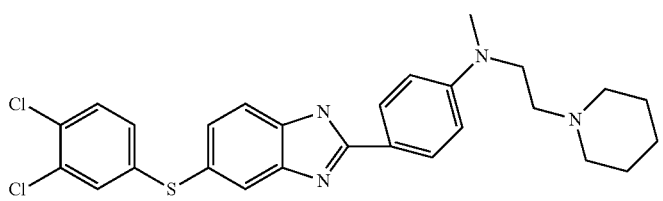 [SMILES: CN(CCN1CCCCC1)c1ccc(-c2nc3cc(Sc4ccc(Cl)c(Cl)c4)ccc3[nH]2)cc1]<br>Benzimidazoles<br>CCR2 IC(50) - 200-300 nM bind |
| SmithKline | 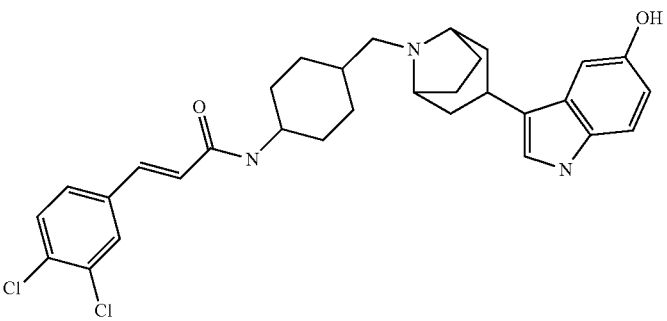 [SMILES: O=C(/C=C/c1ccc(Cl)c(Cl)c1)NC1CCC(CN2C3CCC2CC(c2c[nH]c4ccc(O)cc24)C3)CC1]<br>SB-380732<br>50 nM bind |
| AstraZeneca | AZD-6942<br>29 nM bind; 60 nM taxis |
| Merck | 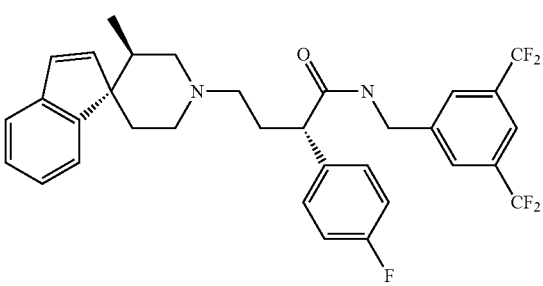<br>41 nM bind; 59 nM taxis |

TABLE 1-continued

| Company | CCR2 Antagonists |
|---|---|
| Teijn/BMS | 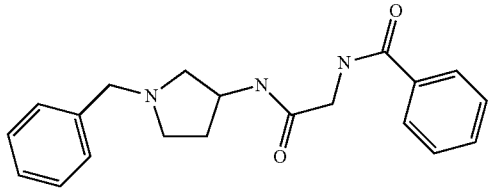 [SMILES: O=C(CNC(=O)c1ccccc1)NC1CCN(Cc2ccccc2)C1]<br>3-Aminopyrrolidines<br>3 nM |
| Telik | 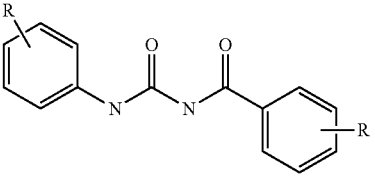 |
| Incyte | 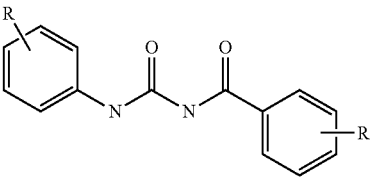<br>INCB-003284 |
| Tocris Biosciences | RS 102895 hydrochloride (Catalog #2089)<br>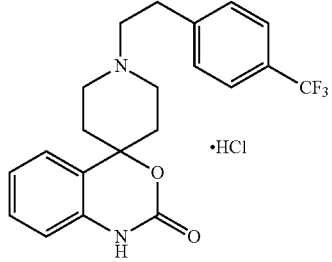 [SMILES: O=C1Nc2ccccc2C2(CCN(CCc3ccc(C(F)(F)F)cc3)CC2)O1 ; Cl]<br>$IC_{50}$ values are 0.36 and 17.8 µM for inhibition of human recombinant CCR2b and CCR1 receptors respectively. Blocks MCP-1-stimulated calcium influx and chemotaxis with $IC_{50}$ values of 32 nM and 1.7 µM respectively. Also inhibits $\alpha_{1A}$; $\alpha_{1D}$ and 5-$HT_{1A}$ receptors. |

In addition, many other CCR2 inhibitors and/or CCR2 antagonists in development are considered to be useful together with the present vaccine, adjuvant, and vaccine treatment regimens. For example, it is anticipated in the present application that the CCR2 inhibitor PF-04178903, would be useful to enhance vaccine response (i.e., enhance antibody titer level production in response to a vaccine containing an adjuvant, or as an adjuvant alone), administered at the same time, before, or after the vaccine is administered to an animal. For example, the present vaccine treatment regimen may comprise administering to an animal an amount of the PF-04178903 as part of (at the same time) a vaccine, after the vaccine, or before the vaccine treatment.

By way of example, the vaccine may be a vaccine for influenza. Standard influenza vaccine preparations are commercially available, and may be used in the practice of this particular example of the vaccine treatment regimen. It is expected that antibody titer levels in an animal treated with this type of vaccine together with the CCR2 antagonist, PF-04178903 or RS1028595, would be 2-fold or higher than a vaccine treatment regimen that did not include the CCR2 antagonist PF-04178903, or RS1028595.

The invention may also be used in the vaccination of an animal for *Staphylococcus*. In particular, the CCR2 inhibitor RS1028595 or PF-04178903, may be included before, at the same time, or after administration of a vaccine containing an immuno-provoking amount of the vaccine.

It is expected that only a routine amount of trial and error would be required in providing such a vaccine treatment regimen by one of ordinary skill in the art of vaccine therapeutics.

Example 16

Small Molecule CCR2 Inhibitor RS102895 Hydrochloride Enhances Antibody Response

The present example is presented to demonstrate the utility of the present invention for enhancing antibody titer levels in vivo in response to vaccination where the treatment includes the small molecule myeloid cell inhibitor, RS102895 (Obtained from Tocris, Catalog number 2089).

Figure 33:
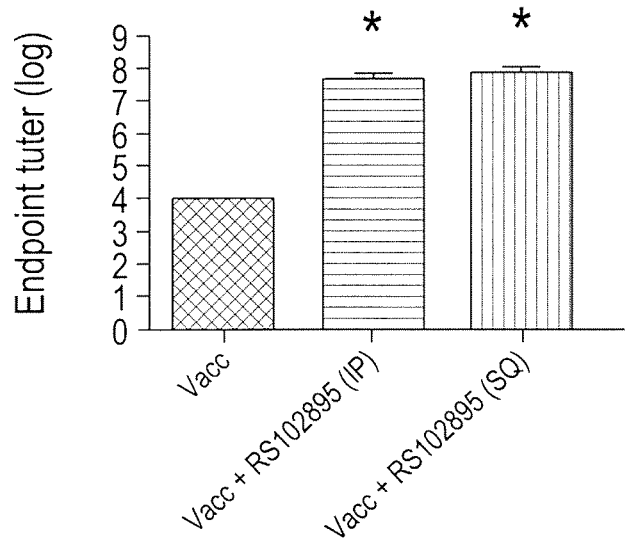
FIG. 33. Effects of co-administration of RS102895 (small molecule inhibitor, Tocris Bioscience), on antibody responses following vaccination via two different modes of administration i.p. (intraperitoneally) or SQ (subcutaneous). Mice were vaccinated SQ with standard vaccine adjuvant (CLDC) and 5 ug ovalbumin, and boosted 10 days later. The first group of mice (n=4 per group) received the vaccine only (cross-hatch bar). A second group of mice was vaccinated and also treated 1 day before, on the same day, and 1 day after with 5 mg/kg of the CCR2 antagonist RS102895 (horizontal line bar), administered i.p. A third group of mice was vaccinated and also treated 1 day before, on the same day, and 1 day after with 5 mg/kg of the CCR2 antagonist RS102895, administered s.c. at the site of vaccination (vertical line bar). Antibody titers to ovalbumin were determined 2 weeks after the boost and plotted as endpoint dilution titers for all animals in all groups. Mice that were vaccinated and treated with RS102895 by either route developed significantly higher antibody titers than mice that received the vaccine alone without the CCR2 antagonist. These data demonstrate the effectiveness of a CCR2 antagonist in increasing immune response as measured by antibody titer level in mice. This enhanced immune response and increase in antibody titer level may be achieved with the administration of the CCR2 antagonist by either an intraperitoneal (IP) (injection into the peritoneum of an animal) or subcutaneous (SQ) administration (under the skin). In addition, administration of the adjuvant additive is demonstrated to be equally as robust administered by either route. Thus, the present adjuvant additives, especially the CCR2 antagonists, may be administered according to techniques routinely used in administering vaccines.

FIG. 33 presents the results obtained with the small molecule inhibitor RS102895 on antibody response in an animal upon vaccination with a representative conventional agent, ova.

Mice were vaccinated subcutaneous (s.c.) with standard vaccine adjuvant (CLDC) (Cationic liposome-DNA complexes) and 5 ug ovalbumin and boosted 10 days later. One group of mice (n=4 per group) received the vaccine only. A second group of mice was vaccinated and also treated 1 day before, on the same day, and 1 day after with 5 mg/kg of the CCR2 antagonist RS102895, administered intra peu i.p. A third group of mice was vaccinated and also treated 1 day before, on the same day, and 1 day after with 5 mg/kg of the CCR2 antagonist RS102895, administered s.c. at the site of vaccination. Antibody titers to ova were determined 2 weeks after the boost and plotted as endpoint dilution titers. Mice that were vaccinated and treated with RS102895 by either route developed significantly higher antibody titers (at least double (2×)) than mice that received the vaccine alone without an adjuvant additive. In additional, the data shows that the enhanced immune response may be achieved through administration of the additive by either IP or SQ administration. (See FIG. 33).

Example 17

Small Molecule CCR2 Inhibitor RS102895 and T Cell Response

The present example demonstrates the effect of the small molecule inhibitor RS 102895 on T cell response in vivo.

Figure 34:
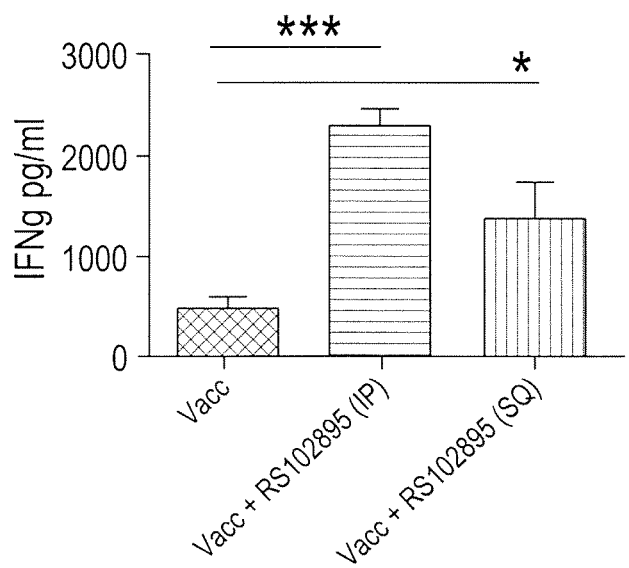
FIG. 34. Effects of co-administration of RS102895 (small molecule inhibitor, Tocris BioSciences), on spleen lymphocyte production of IFN-γ from vaccinated animals (T cell response). Mice were vaccinated s.c. with standard vaccine adjuvant (CLDC) and 5 ug ovalbumin and boosted 10 days later. A first group of mice (n=4 per group) received the vaccine only (cross-hatch). A second group of mice was vaccinated and also treated 1 day before, on the same day, and 1 day after with 5 mg/kg of the CCR2 antagonist RS102895, administered i.p. (horizontal line bar). A third group of mice was vaccinated and also treated 1 day before, on the same day, and 1 day after with 5 mg/kg of the CCR2 antagonist RS102895, administered s.q. at the site of vaccination (vertical line bar). The mice were sacrificed 2 weeks after the booster vaccination and spleen cells were incubated in vitro with ovalbumin (50 ug/ml) for 72 hours. Release of IFY-γ into the supernatants was determined by ELISA. Lymphocytes from mice that were vaccinated and treated with RS102895 by either route produced significantly higher amounts of IFN-γ than lymphocytes from mice that were vaccinated without the RS102895 additive. The data shows IFN-γ production from spleen lymphocutes from vaccinated animals without a CCR2 antagonist was about 450 pg/ml IFN-γ, while with the CCR2 antagonist administered i.p., IFN-γ production was about 2,300 pg/ml. Spleen cells from animals provided the CCR2 antagonist SQ demonstration an IFN-γ production of about 1,400 pg/ml. This data demonstrates that co-administration of RS102895 by either route triggered significantly greater T cell responses to vaccination compared to levels achieved without the RS102895. These data are consistent with the idea that recruitment of inflammatory monocytes during vaccination significantly suppresses vaccine responses.

Mice were vaccinated s.c. with standard vaccine adjuvant (CLDC) and 5 ug ovalbumin and boosted 10 days later. One group of mice (n=4 per group) received the vaccine only. A second group of mice was vaccinated and also treated 1 day before, on the same day, and 1 day after with 5 mg/kg of the CCR2 antagonist RS102895, administered i.p. A third group of mice was vaccinated and also treated 1 day before, on the same day, and 1 day after with 5 mg/kg of the CCR2 antagonist RS102895, administered s.c. at the site of vaccination. The mice were sacrificed 2 weeks after the booster vaccination and spleen cells were incubated in vitro with ovalbumin (50 ug/ml) for 72 hours and release of IFN-γ into the supernatants was determined by ELISA. Lymphocytes from mice that were vaccinated and treated with RS102895 by either route produced significantly higher amounts of IFN-γ than lymphocytes from mice that were vaccinated without RS102895, indicating that co-administration of RS102895 by either route triggered significantly greater T cell responses to vaccination. These data are consistent with the physiological premise that recruitment of inflammatory monocytes during vaccination significantly suppresses vaccine responses. The data from this study is presented at FIG. 34.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims. Tyrosine kinase inhibitors (eg, sunitinib), MDSC differentiating agents (eg, all-trans retinoic acid), reactive nitrogen inhibitors (eg, aminoguanidine or similar drugs); arginase enzyme inhibitors, indoleamine deoxygenase enzyme inhibitors, reactive oxygen species inhibitors, TGF-b inhibitors, IL-10 inhibitors, VEGF inhibitors, and PGE2 synthesis inhibitors.

BIBLIOGRAPHY

All publications, patent applications, and patents mentioned in this specification are herein incorporated by reference to the same extent as if each independent publication, patent, or patent application was specifically and individually indicated to be incorporated by reference. These publications include but are not limited to the references provided below.
1. Affolter V K, Moore P F (2000), Am J Dermatopathol 22:40-48.
2. Affolter V K, Moore P F (2002), Vet Pathol 39:74-83.
3. Agnew, (1994), Chem. Intl. Ed. Engl., 33:183-186.
4. Alves-Rosa F., et al. (2000), Blood 96:2834-2840.
5. Bird R C, et al. (2008), Vet Immunol Immunopathol 123: 289-304.
6. Bucksky P, Egeler R M (1998), Hematol Oncol Clin North Am 12:465-471.
7. Cecchini M G, et al (1987), J Bone Miner Res 2:135-142.
8. Clezardin P, (2003), Curr Med Chem 10:173-180.
9. Dow S W, et al (1998), J Clin Invest 101:2406-2414,
10. Frith J C, et al (2001), Arthritis Rheum 44:2201-2210.
11. Frith J C, Monkkonen J, Blackburn G M, Russell R G, Rogers M J (1997), J. Bone Miner Res 12:1358-1367.
12. Gazzaniga et al. (2007), J. Invest. Dermatol. 127:2031-2041.
13. Gazzaniga S, Bravo A I, Guglielmotti A, van Rooijen N, Maschi F, Vecchi A, Mantovani A, Mordoh J. Wainstok R (2007), J Invest Dermatol 127:2031-2041.
14. Green Jr (2003), Cancer 97:840-847.
15. Howarth D M, Gilchrist G S, Mullan B P, Wiseman G A, Edmonson J H, Schomberg P J (1999) Cancer 85:2278-2290.
16. Hughes D E, Wright K R, Uy H L, Saski A, Yoneda T, Roodman G D, Mundy G R, Boyce B F (1995) J Bone Miner Res 10:147801487.
17. Jordan M B, van Rooijen N, Izui S, Kappler J. Marrack P (2003) Blood 101:594-601.
18. Lauren L, Osterman T, Karhi T (1991). Pharmacol Toxicol 69-365-368.
19. Lehenkari P P, Kellinsalmi M, Napankangas J P, Ylitalo K V Monkkonen J, Rogers M J, Azhayev A, Vaananen H K, Hassinen I E (2002) Mol Pharmacol 61:1255-1262.
20. Lin J H (1996). Bone 18:75-85.
21. Loike J D, Silverstein S C (1983), J Immunol Methods 57:373-379.
22. MacEwen E G, Withrow S J (1996), Saunders Co, Philadelphia, Pa.
23. Mathes M, Jordan M, Dow S (2006), Exp Hematol 34:1393-1402.
24. Monkkonen et al. (1993), Calcif. Tissue Int. 53:139-146.
25. Monkkonen et al. (1994), J. Drug Target, 2:299-308.
26. Moore K J, Matlashewski G (1994). J Immunol 152:2930-2937.
27. Moore P F, Affolter V K, Vernau W (2006), Vet Pathol 43:632-645.
28. Roelofs A J, Thompson K, Gordon S, Rogers M J (2006). Clin Cancer Res 12:6222s-6230s
29. Rogers M J, Gordon S, Benford H L, Coxon F P, Luckman S P, Monkkonen J. Frith J C (2000). Cancer 88:2961-2978
30. Selander K, Lehenkari P, Vaananen H K (1994). Calcif Tissue Int 55:368-375

31. Selander K S, Monkkonen J, Karhukorpi E K, Harkonen P, Hannuniemi R, Vaananen H K (1996). Mol Pharmacol 50:1127-1138
32. Serafini et al. (2006), Semin Cancer Biol. 16:53-65.
33. Skorupski K A, Clifford C A, Paoloni M C, Lara-Garcia A, Barber L, Kent M S, LeBlanc A K, Sabhlok A, Mauldin E A, Shofer F S, Couto C G, Sorenmo K U (2007). J Vet Int Med 21:121-126.
34. Twentyman P R, Luscombe M (1987). Br J Cancer 56:279-285.
35. van Engeland M, Nieland L J, Ramaekers F C, Schutte B, Reutelingsperger C P (1998). Cytometry 31:1-9.
36. van Rooijen N, Kors N (1989). Calcif Tissue Int 45:153-156.
37. van Rooijen N, Kors N, ter Hart H, Claassen E (1988). Virchows Arch B Cell Pathol Incl Mol Pathol 54:241-245
38. Van Rooijen, et al. (1994), J. Immunol. Methods, 174:83-93.
39. Van Rooijen N, Sanders A, Van den Berg T K (1996) J Immunol Methods 193:93-99.
40. Vermes I, Haanen C, Steffens-Nakken H, Reutellingsperger C (1995). J. Immunol. Methods 184:39-51.
41. Villikka K, Perttunen K, Rosnell J, Ikavalko H, Vaho H, Pylkkanen L (2002). Bone 31:418-421.
42. Wellman M L, Krakowka S, Jacobs R M, Kociba G J (1988), In Vitro Cell Dev Biol 24:223-229
43. Zavodovskaya R, Liao A T, Jones C L, Yip B. Chien M B, Moore P F, London C A (2006). Am J Vet Res 67:633-641.
44. Zeisberger et al. (2006), Br. J. Cancer, 95:272-281.
45. Higgins D A, et al. (1996), Vaccine, 14:478-484.
46. Martin J T. (1997), Biologicals, 25:209-213.
47. Banzhoff A, Nacci P, Podda A. (2003), Gerontology, 49:177-184.
48. Segura-Velasquez R, et al. (2006), Vaccine, 24:1073-1080.
49. Suli J, et al. (2004), Vaccine 22:3464-3469.
50. de Souza Matos D C, et al. (2000). Vaccine, 18:2125-2131.
51. Peng M, et al. (2006), Vaccine, 24:887-896.
52. Qin W. et al. (2004), Cell Mol Immunol, 1:148-152.
53. Sung J I, et al. (2006), Curr Opin Mol Ther 8:150-155.
54. Jaganathan K S, et al. (2006), Vaccine, 24:4201-4211.
55. Sugai T. et al. (2005), Vaccine, 23:5450-5456.
56. Theeten H, et al. (2005), Vaccine, 23:1515-1521.
57. Caglar K, et al. (2005), APMIS, 113:256-263.
58. Flick-Smith H C, et al. (2002), Infect. Immun. 70:2022-2028.
59. Petrik M S, et al. (2007), Neuromolecular Med. 9:83-100.
60. Levesque P M, et al. (2006), Hum. Vaccin. 2:74-77.
61. Hedlund J. et al. (2002). Vaccine 20:164-169.
62. Sen G. et al. (2006). Infect. Immun. 74:2177-2186.
63. Sabirov A, Metzger D W. (2006), Vaccine, 24:5584-5592.
64. Pimenta F C, et al. (2006), Infect. Immun., 74:4939-4944.
65. Mullen G E D, et al. (2006), Vaccine, 24:2497-2505.
66. Langermans J A M, et al. (2005), Vaccine, 23:4935-4943.
67. Stewart V A, et al. (2006), Vaccine, 24:6483-6492.
68. Brando C, et al. (2006), Infect. Immun. Epub.
69. Rosado-Vallado M, et al. (2005), Vaccine, 23:5372-5379.
70. Kenney R T, et al. (1999), J. Immunol., 163:4481-4488.
71. Mendez S, et al. (2003), Infect. Immun., 71:5121-5129.
72. Vitetta E S, et al. (2006), Proc. Nat. Acad. Sci. (USA), 103:2268-2273.
73. Griffiths G D, et al. (1997) Vaccine, 15:1933-1939.
74. Kende M. et al. (2006), Vaccine, 24:2213-2221.
75. Eldridge J H, et al. (1991), Infect. Immun., 59:2978-2986.
76. Desai M P, et al. (2000), J. Microencapsul., 17:215-225.
77. Palese (2006), Emerg. Inf. Dis., 12 (1): 61-65.
78. Caughey, B. and Baron, G. S. (2006), Nature (443(19): 803-810.
79. Aguzzi, A. and Heikenwalder. M. (2006), Nature Reviews/Microbiology, 4:765-775.
80. A. Aguzzi, F. L. et al. (2003), Br Med Bull 66: 141-159.
81. D. Peretz, et al (2001), Nature 412: 739-743.
82. M. Enari, et al. (2001), Proc Natl Acad Sci USA 98: 9295-9299.
83. Polymenidou M, et al. (2004), Proc Natl Acad Sci USA, 101(Suppl. 2): 14670-14676.
84. M. F. Koller, T. et al. (2002), J Neuroimmunol 132: 113-116.
85. E. M. Sigurdsson, et al. (2002), Am J Pathol 161: 13-17.
86. S. Gulch, F. et al. (2003), J Biol Chem 278: 18524-18531.
87. E. Hanan, O. et al. (2001), Biochem Biophys Res Commun 280: 115-120.
88. E. Hanan, et al. (2001), Cell Mol Neurobiol 21: 693-703.
89. L. Souan, et al. (2001), Eur J Immunol 31: 2338-2346.
90. M. Arbel, et al. (2003), J Neuroimmunol 144: 38-45.
91. A. Schwarz, et al. (2003), Neurosci Lett 350: 187-189.
92. M. B. Rosset, et al. (2004), J Immunol 172: 5168-5174.
93. H. Nakano et al. (2009), Nature Immunology, 10(4): 394-402.
94. Higgins et al. (2007), Chemokine Biology—Basic Research an Clinical Application, Vol. II, Birkhauser Verlag Basel Switzerland, "Small molecule CCR2 antagonists", pg. 115-123.
95. Clark et al (1983), J. Med. Chem. 26 657.
96. Mirzadegan et al (2000), J. Biol. Chem. 275 25562.

What is claimed is:

1. A method for enhancing immune response to a vaccine in an animal comprising:
    administering a vaccine to an animal; and
    inhibiting migration of myeloid cells by administering a myeloid derived suppressor cell inhibiting agent to the animal, to provide a treated animal, wherein the myeloid derived suppressor cell inhibiting agent is a CCR2 inhibitor.

2. The method of claim 1 wherein the enhanced immune response is demonstrated in the treated animal as an elevated antibody titer level in vivo.

3. The method of claim 1 wherein the myeloid derived suppressor cell inhibiting agent is administered to the animal before, at the same time, or after the administration of the vaccine.

4. The method of claim 1 wherein the CCR2 inhibitor is a small molecule.

5. The method of claim 1 wherein the vaccine contains alum, incomplete Freunds adjuvant, Corrixa MPL adjuvant, liposomal polyI:C adjuvant or cationic liposome-DNA complex adjuvant.

6. The method of claim 1, wherein the CCR2 inhibitor is RS 1028595 or PF-04178903.

* * * * *